(12) United States Patent
Levinson et al.

(10) Patent No.: US 8,523,927 B2
(45) Date of Patent: Sep. 3, 2013

(54) SYSTEM FOR TREATING LIPID-RICH REGIONS

(75) Inventors: Mitchell E. Levinson, Pleasanton, CA (US); Jesse N. Rosen, Albany, CA (US); Corydon A. Hinton, Oakland, CA (US)

(73) Assignee: Zeltiq Aesthetics, Inc., Pleasanton, CA (US)

( * ) Notice: Subject to any disclaimer, the term of this patent is extended or adjusted under 35 U.S.C. 154(b) by 1633 days.

(21) Appl. No.: 11/777,992

(22) Filed: Jul. 13, 2007

(65) Prior Publication Data

US 2009/0018623 A1   Jan. 15, 2009

(51) Int. Cl.
*A61F 7/00*   (2006.01)

(52) U.S. Cl.
USPC .............. 607/96; 607/104; 607/108; 606/20

(58) Field of Classification Search
USPC ................ 607/96, 104, 108–112; 606/20, 606/22–26
See application file for complete search history.

(56) References Cited

U.S. PATENT DOCUMENTS

| | | | |
|---|---|---|---|
| 681,806 A | 9/1901 | Mignault |
| 889,810 A | 6/1908 | Robinson |
| 2,516,491 A | 7/1950 | Swastek |
| 2,766,619 A | 10/1956 | Tribus et al. |
| 3,093,135 A | 6/1963 | Hirschhorn |
| 3,132,688 A | 5/1964 | Nowak |
| 3,282,267 A | 11/1966 | Wiliam |
| 3,502,080 A | 3/1970 | Hirschhorn |
| 3,587,577 A | 6/1971 | Smirnov et al. |
| 3,591,645 A | 7/1971 | Selwitz |
| 3,703,897 A | 11/1972 | Mack et al. |
| 3,710,784 A | 1/1973 | Taylor |
| 3,786,814 A | 1/1974 | Armao |
| 3,827,436 A | 8/1974 | Stumpf et al. |
| 3,942,519 A | 3/1976 | Shock |
| 3,948,269 A | 4/1976 | Zimmer |
| 3,986,385 A | 10/1976 | Johnston et al. |
| 4,002,221 A | 1/1977 | Buchalter |
| 4,140,130 A | 2/1979 | Storm, III |
| 4,178,429 A | 12/1979 | Scheffer |
| 4,202,336 A | 5/1980 | van Gerven et al. |
| 4,266,043 A | 5/1981 | Fujii et al. |
| 4,381,009 A | 4/1983 | Del Bon et al. |
| 4,396,011 A | 8/1983 | Mack et al. |
| 4,483,341 A | 11/1984 | Witteles |

(Continued)

FOREIGN PATENT DOCUMENTS

| | | |
|---|---|---|
| CN | 1511503 | 7/2004 |
| CN | 1741777 | 3/2006 |

(Continued)

OTHER PUBLICATIONS

U.S. Appl. No. 12/196,246, filed Aug. 21, 2008, Levinson.

(Continued)

*Primary Examiner* — Ahmed Farah
(74) *Attorney, Agent, or Firm* — Perkins Coie LLP

(57) ABSTRACT

A system is described for removing heat from a subject's subcutaneous lipid-rich regions, such as tissues, organs, cells, and so forth. In various embodiments, the system includes a controller, a computing device, a data acquisition device, a chiller, and one or more applicators. The system can employ these components to receive a selection of a treatment profile and apply the selected treatment using an applicator. The treatment profile may be received from a patient protection device that connects to an applicator.

30 Claims, 10 Drawing Sheets

(56) References Cited

U.S. PATENT DOCUMENTS

| | | |
|---|---|---|
| 4,528,979 A | 7/1985 | Marchenko et al. |
| 4,531,524 A | 7/1985 | Mioduski |
| 4,548,212 A | 10/1985 | Leung |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt et al. |
| 4,741,338 A | 5/1988 | Miyamae et al. |
| 4,764,463 A | 8/1988 | Mason et al. |
| 4,802,475 A | 2/1989 | Weshahy et al. |
| 4,832,022 A | 5/1989 | Tjulkov et al. |
| 4,846,176 A | 7/1989 | Golden |
| 4,850,340 A | 7/1989 | Onishi |
| 4,869,250 A | 9/1989 | Bitterly |
| 4,880,564 A | 11/1989 | Abel et al. |
| 4,906,463 A | 3/1990 | Cleary et al. |
| 4,930,317 A | 6/1990 | Klein |
| 4,935,345 A | 6/1990 | Guilbeau et al. |
| 4,961,422 A | 10/1990 | Marchosky et al. |
| 4,962,761 A | 10/1990 | Golden |
| 4,990,144 A | 2/1991 | Blott |
| 5,007,433 A | 4/1991 | Hermsdorffer et al. |
| 5,018,521 A | 5/1991 | Campbell |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen et al. |
| 5,143,063 A | 9/1992 | Fellner |
| 5,148,804 A | 9/1992 | Hill et al. |
| 5,169,384 A | 12/1992 | Bosniak et al. |
| 5,197,466 A | 3/1993 | Marchosky et al. |
| 5,207,674 A | 5/1993 | Hamilton |
| 5,221,726 A | 6/1993 | Dabi et al. |
| 5,264,234 A | 11/1993 | Windhab et al. |
| 5,277,030 A | 1/1994 | Miller |
| 5,314,423 A | 5/1994 | Seney |
| 5,330,745 A | 7/1994 | McDow |
| 5,334,131 A | 8/1994 | Omandam et al. |
| 5,336,616 A | 8/1994 | Livesey et al. |
| 5,339,541 A | 8/1994 | Owens |
| 5,342,617 A | 8/1994 | Gold |
| 5,351,677 A | 10/1994 | Kami et al. |
| 5,362,966 A | 11/1994 | Rosenthal et al. |
| 5,363,347 A | 11/1994 | Nguyen |
| 5,427,772 A | 6/1995 | Hagan |
| 5,433,717 A | 7/1995 | Rubinsky et al. |
| 5,456,703 A | 10/1995 | Beeuwkes, III |
| 5,472,416 A | 12/1995 | Blugerman et al. |
| 5,497,596 A | 3/1996 | Zatkulak |
| 5,505,726 A | 4/1996 | Meserol |
| 5,505,730 A | 4/1996 | Edwards |
| 5,507,790 A | 4/1996 | Weiss et al. |
| 5,514,105 A | 5/1996 | Goodman, Jr. et al. |
| 5,514,170 A | 5/1996 | Mauch |
| 5,531,742 A | 7/1996 | Barken |
| 5,562,604 A | 10/1996 | Yablon et al. |
| 5,571,801 A | 11/1996 | Segall et al. |
| 5,603,221 A | 2/1997 | Maytal et al. |
| 5,628,769 A | 5/1997 | Saringer et al. |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |
| 5,654,546 A | 8/1997 | Lindsay |
| 5,660,836 A | 8/1997 | Knowlton |
| 5,672,172 A | 9/1997 | Zupkas |
| 5,733,280 A | 3/1998 | Avitall |
| 5,741,248 A | 4/1998 | Stern et al. |
| 5,746,736 A | 5/1998 | Tankovich |
| 5,755,663 A | 5/1998 | Larsen et al. |
| 5,755,753 A | 5/1998 | Knowlton |
| 5,759,182 A | 6/1998 | Varney et al. |
| 5,759,764 A | 6/1998 | Polovina |
| 5,769,879 A | 6/1998 | Richards et al. |
| 5,785,955 A | 7/1998 | Fischer |
| 5,817,050 A | 10/1998 | Klein |
| 5,830,208 A | 11/1998 | Muller |
| 5,833,685 A | 11/1998 | Tortal et al. |
| 5,844,013 A | 12/1998 | Kenndoff et al. |
| 5,871,524 A | 2/1999 | Knowlton |
| 5,871,526 A | 2/1999 | Gibbs et al. |
| 5,895,418 A | 4/1999 | Saringer et al. |
| 5,901,707 A | 5/1999 | Gon.cedilla.alves et al. |
| 5,902,256 A | 5/1999 | Benaron |
| 5,919,219 A | 7/1999 | Knowlton |
| 5,944,748 A | 8/1999 | Mager et al. |
| 5,948,011 A | 9/1999 | Knowlton |
| 5,964,092 A | 10/1999 | Tozuka et al. |
| 5,964,749 A | 10/1999 | Eckhouse et al. |
| 5,967,976 A | 10/1999 | Larsen et al. |
| 5,986,167 A | 11/1999 | Arteman et al. |
| 6,017,337 A | 1/2000 | Pira et al. |
| 6,023,932 A | 2/2000 | Johnston et al. |
| 6,032,675 A | 3/2000 | Rubinsky |
| 6,039,694 A | 3/2000 | Larson et al. |
| 6,041,787 A | 3/2000 | Rubinsky |
| 6,049,927 A | 4/2000 | Thomas et al. |
| 6,051,159 A | 4/2000 | Hao et al. |
| 6,074,415 A | 6/2000 | Der Ovanesian |
| 6,093,230 A | 7/2000 | Johnson, III et al. |
| 6,102,885 A | 8/2000 | Bass |
| 6,120,519 A | 9/2000 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung et al. |
| 6,350,276 B1 | 2/2002 | Knowlton |
| 6,354,297 B1 | 3/2002 | Eiseman |
| 6,357,907 B1 | 3/2002 | Cleveland et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,954 B1 | 8/2002 | Goetz et al. |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |
| 6,494,844 B1 | 12/2002 | Van Bladel et al. |
| 6,519,964 B2 | 2/2003 | Bieberich |
| 6,523,354 B1 | 2/2003 | Tolbert |
| 6,527,765 B2 | 3/2003 | Kelman et al. |
| 6,544,248 B1 | 4/2003 | Bass |
| 6,548,297 B1 | 4/2003 | Kuri-Harcuch et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,592,577 B2 | 7/2003 | Abboud et al. |
| 6,605,080 B1 | 8/2003 | Altshuler et al. |
| 6,626,854 B2 | 9/2003 | Friedman et al. |
| 6,635,053 B1 | 10/2003 | Lalonde et al. |
| 6,645,162 B2 | 11/2003 | Friedman et al. |
| 6,645,229 B2 | 11/2003 | Matsumura et al. |
| 6,648,904 B2 | 11/2003 | Altshuler et al. |
| 6,699,266 B2 | 3/2004 | Lachenbruch et al. |
| 6,718,785 B2 | 4/2004 | Bieberich |
| 6,741,895 B1 | 5/2004 | Gafni et al. |

| | | |
|---|---|---|
| 6,746,474 B2 | 6/2004 | Saadat |
| 6,749,624 B2 | 6/2004 | Knowlton |
| 6,764,502 B2 | 7/2004 | Bieberich |
| 6,789,545 B2 | 9/2004 | Littrup et al. |
| 6,820,961 B2 | 11/2004 | Johnson |
| 6,821,274 B2 | 11/2004 | McHale et al. |
| 6,840,955 B2 | 1/2005 | Ein |
| 6,878,144 B2 | 4/2005 | Altshuler et al. |
| 6,904,956 B2 | 6/2005 | Noel |
| 6,918,903 B2 | 7/2005 | Bass |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 7,005,558 B1 | 2/2006 | Johansson et al. |
| 7,022,121 B2 | 4/2006 | Stern et al. |
| 7,037,326 B2 | 5/2006 | Lee et al. |
| 7,077,858 B2 | 7/2006 | Fletcher et al. |
| 7,081,111 B2 | 7/2006 | Svaasand et al. |
| 7,096,204 B1 | 8/2006 | Chen et al. |
| 7,112,712 B1 | 9/2006 | Ancell |
| 7,115,123 B2 | 10/2006 | Knowlton et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,367,341 B2 | 5/2008 | Anderson et al. |
| 7,713,266 B2 | 5/2010 | Elkins et al. |
| 7,854,754 B2 | 12/2010 | Ting et al. |
| 2001/0031459 A1 | 10/2001 | Fahy et al. |
| 2001/0039439 A1 | 11/2001 | Elkins et al. |
| 2001/0045104 A1 | 11/2001 | Bailey et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0103520 A1 | 8/2002 | Latham |
| 2002/0117293 A1 | 8/2002 | Campbell |
| 2002/0120315 A1 | 8/2002 | Furuno et al. |
| 2002/0151887 A1 | 10/2002 | Stern et al. |
| 2002/0188286 A1 | 12/2002 | Quijano et al. |
| 2003/0044764 A1 | 3/2003 | Soane et al. |
| 2003/0055414 A1 | 3/2003 | Altshuler et al. |
| 2003/0069618 A1 | 4/2003 | Smith et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0125649 A1 | 7/2003 | McIntosh et al. |
| 2003/0199226 A1 | 10/2003 | Sommer et al. |
| 2003/0220674 A1 | 11/2003 | Anderson et al. |
| 2003/0236487 A1 | 12/2003 | Knowlton |
| 2004/0006328 A1 | 1/2004 | Anderson |
| 2004/0009936 A1 | 1/2004 | Tang et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0093042 A1 | 5/2004 | Altshuler et al. |
| 2004/0104012 A1 | 6/2004 | Zhou et al. |
| 2004/0162596 A1 | 8/2004 | Altshuler et al. |
| 2004/0176667 A1 | 9/2004 | Mihai et al. |
| 2004/0199226 A1 | 10/2004 | Shadduck |
| 2004/0206365 A1 | 10/2004 | Knowlton |
| 2004/0210214 A1 | 10/2004 | Knowlton |
| 2004/0210287 A1 | 10/2004 | Greene |
| 2004/0259855 A1 | 12/2004 | Anderson et al. |
| 2005/0033957 A1 | 2/2005 | Enokida |
| 2005/0049661 A1 | 3/2005 | Koffroth |
| 2005/0154431 A1 | 7/2005 | Quistgaard et al. |
| 2005/0159986 A1 | 7/2005 | Breeland et al. |
| 2005/0182462 A1 | 8/2005 | Chornenky et al. |
| 2005/0187597 A1 | 8/2005 | Vanderschuit |
| 2005/0222565 A1 | 10/2005 | Manstein |
| 2005/0251120 A1 | 11/2005 | Anderson et al. |
| 2005/0283144 A1 | 12/2005 | Shiono et al. |
| 2006/0030778 A1 | 2/2006 | Mendlein et al. |
| 2006/0036300 A1 | 2/2006 | Kreindel |
| 2006/0041704 A1 | 2/2006 | Choi |
| 2006/0074313 A1 | 4/2006 | Slayton et al. |
| 2006/0079852 A1 | 4/2006 | Bubb et al. |
| 2006/0106836 A1 | 5/2006 | Masugi et al. |
| 2006/0122509 A1 | 6/2006 | Desilets |
| 2006/0200063 A1 | 9/2006 | Munro et al. |
| 2006/0234899 A1 | 10/2006 | Nekmard et al. |
| 2006/0265032 A1 | 11/2006 | Hennings et al. |
| 2006/0270745 A1 | 11/2006 | Hunt et al. |
| 2006/0293734 A1 | 12/2006 | Scott et al. |
| 2007/0010861 A1 | 1/2007 | Anderson et al. |
| 2007/0032561 A1 | 2/2007 | Lin et al. |
| 2007/0129714 A1 | 6/2007 | Elkins et al. |
| 2007/0141265 A1 | 6/2007 | Thomson |
| 2007/0198071 A1 | 8/2007 | Ting et al. |
| 2007/0239075 A1 | 10/2007 | Rosenberg et al. |
| 2007/0249519 A1 | 10/2007 | Guha et al. |
| 2007/0255187 A1 | 11/2007 | Branch |
| 2007/0255362 A1 | 11/2007 | Levinson et al. |
| 2007/0270925 A1 | 11/2007 | Levinson |
| 2007/0282249 A1 | 12/2007 | Quisenberry et al. |
| 2007/0282318 A1 | 12/2007 | Spooner et al. |
| 2008/0046047 A1 | 2/2008 | Jacobs |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0140371 A1 | 6/2008 | Warner |
| 2008/0183164 A1 | 7/2008 | Elkins et al. |
| 2008/0287839 A1 | 11/2008 | Rosen et al. |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0118722 A1 | 5/2009 | Ebbers et al. |
| 2009/0149929 A1 | 6/2009 | Levinson et al. |
| 2009/0149930 A1 | 6/2009 | Schenck |
| 2009/0312676 A1 | 12/2009 | Rousso et al. |
| 2010/0081971 A1 | 4/2010 | Allison |
| 2010/0152824 A1 | 6/2010 | Alison |
| 2010/0280582 A1 | 11/2010 | Baker et al. |
| 2011/0077723 A1 | 3/2011 | Parish et al. |
| 2012/0022518 A1 | 1/2012 | Levinson |
| 2012/0239123 A1 | 9/2012 | Weber |
| 2013/0066309 A1 | 3/2013 | Levinson |

FOREIGN PATENT DOCUMENTS

| | | |
|---|---|---|
| CN | 1817990 A | 8/2006 |
| DE | 532976 C | 9/1931 |
| DE | 2851602 | 6/1980 |
| DE | 4213584 A1 | 11/1992 |
| DE | 4224595 | 1/1994 |
| EP | 0263069 A2 | 4/1988 |
| EP | 0397043 | 11/1990 |
| EP | 0406244 A1 | 1/1991 |
| EP | 0598824 A1 | 6/1994 |
| EP | 1201266 | 5/2002 |
| FR | 2745935 | 9/1997 |
| GB | 2286660 A | 8/1995 |
| GB | 2323659 A | 9/1998 |
| JP | S6282977 | 4/1987 |
| JP | 63076895 | 4/1988 |
| JP | 63076895 A | 4/1988 |
| JP | 03051964 | 3/1991 |
| JP | 3259975 A | 11/1991 |
| JP | 4093597 A | 3/1992 |
| JP | 7194666 | 8/1995 |
| JP | 7268274 | 10/1995 |
| JP | 7268274 A | 10/1995 |
| JP | 09164163 A | 6/1997 |
| JP | 10216169 A | 8/1998 |
| JP | 3065657 | 11/1999 |
| JP | A2000503154 | 3/2000 |
| JP | A2002543668 | 12/2002 |
| JP | A2004013600 | 1/2004 |
| JP | 2004073812 | 11/2004 |
| JP | A2005039790 | 2/2005 |

| | | |
|---|---|---|
| JP | 3655820 | 3/2005 |
| JP | 200565984 | 3/2005 |
| JP | 2005110755 | 4/2005 |
| JP | 2005520608 T | 7/2005 |
| JP | 2008323716 | 11/2005 |
| JP | 2006026001 A | 2/2006 |
| JP | A2006520949 | 9/2006 |
| JP | 2008532591 | 8/2008 |
| KR | 1020040094508 | 11/2004 |
| SU | 532976 | 11/1978 |
| TW | 0476644 | 2/2002 |
| WO | WO8503216 | 8/1985 |
| WO | WO94/04116 | 3/1994 |
| WO | WO-1994004116 | 3/1994 |
| WO | WO-96/37158 | 11/1996 |
| WO | WO-9636293 A1 | 11/1996 |
| WO | WO-97/05828 | 2/1997 |
| WO | WO-9722262 A2 | 6/1997 |
| WO | WO-9725798 | 7/1997 |
| WO | WO-98/41157 | 9/1998 |
| WO | WO-9841156 | 9/1998 |
| WO | WO-9938469 A1 | 8/1999 |
| WO | WO-00/44346 | 8/2000 |
| WO | WO0044346 | 8/2000 |
| WO | WO-0065770 | 11/2000 |
| WO | WO0067685 | 11/2000 |
| WO | WO0114012 | 3/2001 |
| WO | WO-02/05736 A2 | 1/2002 |
| WO | WO0205736 | 1/2002 |
| WO | WO-02/102921 | 12/2002 |
| WO | WO02102921 | 12/2002 |
| WO | WO-03/078596 A3 | 9/2003 |
| WO | WO03007859 | 9/2003 |
| WO | WO-03078596 | 9/2003 |
| WO | WO-2004/000098 | 12/2003 |
| WO | WO-2004080279 A2 | 9/2004 |
| WO | WO-2005046540 A1 | 5/2005 |
| WO | WO-2005096979 | 10/2005 |
| WO | WO-2006/066226 | 6/2006 |
| WO | WO2006094348 | 9/2006 |
| WO | WO-2006/127467 | 11/2006 |
| WO | WO-2007012083 | 1/2007 |
| WO | WO-2007041642 A2 | 4/2007 |
| WO | WO2007127924 | 11/2007 |
| WO | WO2008039557 | 4/2008 |
| WO | WO2008143678 | 11/2008 |
| WO | WO2009026471 | 2/2009 |
| WO | WO2010077841 | 7/2010 |
| WO | WO2010127315 | 11/2010 |
| WO | WO2012012296 | 1/2012 |
| WO | WO2012103242 | 8/2012 |

OTHER PUBLICATIONS

U.S. Appl. No. 12/275,002, filed Nov. 20, 2008, Martens.
U.S. Appl. No. 12/275,014, filed Nov. 20, 2008, Martens.
U.S. Appl. No. 12/337,544, filed Dec. 17, 2008, Alison.
Bohm et al., "Saline-enhanced radiofrequency ablation of breat tissue: an in vitro feasibility study," Invest Radiol, 2000, pp. 149-157, vol. 35—issue (3).
Disclosure re: "Method and Apparatus for Regional Fat Reduction Using Controlled and Sustained Cooling of Skin Surface".
Donski et al., "The Effects of Cooling No Experimental Free Flap Survival," Brit J Plas Surg, 1980, pp. 353-360, vol. 33.
Hale et al., "Influence of chronic heat exposure and prolonged food deprivation on execretion of mahnesium, phosphorus, calcium, hydrogen ion & ketones," Aerosp Med, 1968, pp. 919-926, vol. 39—issue (9).
International Search Report and Written Opinion for PCT/US2007/023492; Applicant: Zeltiq Aesthetics, Inc.; Date of Mailing: May 15, 2008, 7 pages.
International Search Report and Written Opinion for PCT/US2007/062508; Applicant: Juniper Medical, Inc.; Date of Mailing: Jul. 20, 2007, 13 pages.
International Search Report and Written Opinion for PCT/US2007/064016; Applicant: Juniper Medical, Inc.; Date of Mailing: Jul. 20, 2007, 13 pages.
International Search Report and Written Opinion for PCT/US2007/064017; Applicant: Juniper Medical, Inc.; Date of Mailing: Oct. 26, 2007, 16 pages.
International Search Report and Written Opinion for PCT/US2007/064018; Applicant: Juniper Medical, Inc.; Date of Mailing: Jul. 26, 2007, 13 pages.
International Search Report and Written Opinion for PCT/US2007/067638; Applicant: Juniper Medical, Inc.; Date of Mailing: Jan. 10, 2008, 11 pages.
International Search Report and Written Opinion for PCT/US2007/069694; Applicant: Juniper Medical, Inc.; Date of Mailing: Nov. 23, 2007, 12 pages.
International Search Report and Written Opinion for PCT/US2007/083255; Applicant: Zeltiq Aesthetics, Inc.; Date of Mailing: Aug. 11, 2008, 8 pages.
International Search Report and Written Opinion for PCT/US2008/073930; Applicant: Zeltiq Aesthetics, Inc.; Date of Mailing: Nov. 7, 2008, 10 pages.
International Search Report for EP07758558.6; Applicant: Zeltiq Aesthetics, Inc.; Mailed on Jul. 20, 2007, 4 pages.
International Search Report for PCT/US2005/045988; (Apr. 25, 2006).
Kundu et al., "Breath acetone analyzer: diagnostic tool to monitor dietary fat loss," Clin Chem, 1993, pp. 87-92, vol. 39, issue (1).
Kundu et al., "Novel solid-phase assay of ketone bodies in urine," Clin Chem, 1991, pp. 1565-1569, vol. 37—issue (9).
Kuroda et al., "Thermal distribution of radio-frequency inductive hyperthermia using an inductive aperture-type applicator: evaluation of the effect of tumour size and depth," Med Biol Eng Comput, 1999, pp. 285-290, vol. 37—issue (3).
Levchenko, et al., "Effect of dehydration on lipid metabolism," WMJ, 1978, pp. 95-97, vol. 50—issue (1).
Lidagoster, MD et al., "Comparison of Autologous Fat Transfer in Fresh, Refrigerated, and Frozen Specimens: An Animal Model Presented," at the 16th Annual Meeting of the Northeastern Society of Plastic Surgeons: Burlington, VT, 1999, pp. 512-515.
Lvova, "Lipid levels and lipid peroxidation in frog tissues during hypothermia and hibernation," WMJ, 1990, pp. 65-70, vol. 62—issue (1).
Nagao et al., "Dietary diacylglycerol suppresses accumulation of body fat compared to triacylglycerol in men a double-blind controlled trial," J Nutr, 2000, pp. 792-797, vol. 130—issue (4).
Nielsen, "Thermoregulation in Rest and Exercise," Acta Phys Scan Supp, 1969, pp. 6-74, vol. 323.
Non-Final Office Action; U.S. Appl. No. 11/435,502; Date of Mailing: Jul. 17, 2009, 10 pages.
Peterson et al., "Bilateral Fat Necrosis of the Scrotum, Urology Service, Department of Surgery, Dermatology Service, Department of Medicine and Department of Pediatrics," Letterman Army Medical Center, Journal of Urology, 1976, pp. 825-826, vol. 116, The Williams & Wilkins Co.
Schoning, et al., "Experimental Frostbite: Freezing Times, Rewarming Times, and Lowest Temperatures of Pig Skin Exposed to Chilled Air," Cryobiology, 1990, pp. 189-193, 27.
U.S. Appl. No. 11/425,502, filed May 17, 2006, Levinson.
U.S. Appl. No. 11/528,189, filed Sep. 26, 2006, Levinson et al.
U.S. Appl. No. 11/528,225, filed Sep. 26, 2006, Levinson et al.
U.S. Appl. No. 11/741,271, filed Apr. 27, 2007, Levinson et al.
U.S. Appl. No. 11/750,953, filed May 18, 2007, Rosen et al.
U.S. Appl. No. 11/777,995, filed Jul. 13, 2007, Levinson et al.
U.S. Appl. No. 11/777,999, filed Jul. 13, 2007, Levinson et al.
U.S. Appl. No. 11/778,001, filed Jul. 13, 2007, Levinson et al.
U.S. Appl. No. 11/778,003, filed Jul. 13, 2007, Levinson et al.
Ardevol et al., "Cooling rates of tissue samples during freezing with liquid nitrogen," J. of Biochem and Biophysical Methods, Aug. 1993, 27:77-86, Elsevier Science Publishers B.V.
Bondei et al., "Disorders of Subcutaneous Tissue (Cold Panniculitis)," Dermatology in General Medicine, Fourth Edition, vol. 1, Chapter 108, 1993, Section 16, pp. 1333-1334.
Burge et al., "Hair Follicle Destruction and Regeneration in Guinea Pig Skin after Cutaneous Freeze Injury," Cryobiology, 1990, 27(2):153-163.

Duncan et al., "Cold Panniculitis," Arch. Derm., Dec. 1966, 94:722-24.
Epstein et al., "Popsicle Panniculitis," The New England Journal of Medicine, Apr. 23, 1970, 282(17):966-67.
Gage "Current Progress in Cryosurgery," Cryobiology 25, 1988, pp. 483-486.
Heller-Page et al., "Temperature-dependent skin disorders," Journal of the American Academy of Dermatology, May 1988, vol. 18, No. 5, Pt 1, pp. 1003-1019.
Hemmingsson et al, "Attenuation in Human Muscle and Fat Tissue in Vivo and in Vitro," Acta Radiologica Diagnosis, 1982, 23, 149-151.
Henry et al., "Les Dermatoses Hivemales," Rev Med Liege, 1999, 54:11, 864-866. [Abstract Attached].
Holman et al., "Variation in Cryolesion Penetration Due to Probe Size and Tissue Thermal Conductivity," The Annals of Thoracic Surgery, 1992, vol. 53, pp. 123-126.
Hong et al., "Patterns of Ice Formation in Normal and Malignant Breast Tissue," Cryobiology 31, 1994, pp. 109-120.
Kellum et al., "Sclerema Neonatorum: Report of Case and Analysis of Subcutaneous and Epidermal-Dermal Lipids by Chromatographic Methods," Arch. Derm., Apr. 1968, 97:372-80.
Koska et al., "Endocrine Regulation of Subcutaneous Fat Metabolism During Cold Exposure in Humans," Ann. N.Y. Acad, Sci., 2002, 967:500-05.
Laugier et al., "In Vivo Results with a New Device for Ultrasonic Monitoring of Pig Skin Cryosurgery: The Echographic Cryprobe," The Society for Investigative Dermatology, Inc., Aug. 1998, vol. 111, No. 2, pp. 314-319.
Maize, J.C., "Panniculitis," Cutaneous Pathology, Chapter 13: 327-344, 1998.
Malcom et al., "Fatty acid composition of adipose tissue in humans: differences between subcutaneous sites," Am. J. Clin. Nutr., 1989, 50:288-91.
Moschella et al., "Diseases of the Subcutaneous Tissue," Dermatology, 1985, Second Ed., vol. 2, Chapter 19, Section II, pp. 1169-1181, W. B. Saunders Company.
Murphy et al., "Frostbite: Pathogensesis and Treatment," The Journal of Trauma: Injury, Infection, and Critical Care, Jan. 2000, 48(1):171-178.
Nagore et al., "Lipoatrophia semicircularis—a traumatic panniculitis: Report of seven cases and review of the literature," Journal of the American Academy of Dermatology, Nov. 1998, 39:879-81.
Pease et al., "An Integrated Probe for Magnetic Resonance Imaging Monitored Skin Cryosurgery," Journal of Biomedical Engineering, Feb. 1995, vol. 117, No. 1, pp. 59-63.
Pech et al., "Attenuation values, volume changes and artifacts in tissue due to freezing," Acta Radiologica 6, Nov.-Dec. 1987, 28(6):779-82.
Phinney et al., "Human Subcutaneous Adipose Tissue Shows Site-Specific Differences in Fatty Acid Composition," Am. J. Clin. Nutr., 1994, 60:725-29.
Rabi et al., "Metabolic adaptations in brown adipose tissue of the hamster in extreme ambient temperatures," American Journal of Physiology, Jul. 1976, vol. 231, Issue 1, pp. 153-160.
Renold, A.E., "Adipose Tissue," Handbook of Physiology, American Physiological Society, 1965, Chapter 15, pp. 170-176.
Rubinsky et al., "Cryosurgery: advances in the application of low temperatures to medicine," International Journal of Refrigeration, Jul. 1991, 14(4):190-199.
Shephard, "Adaptation to Exercise in the Cold," Sports Medicine, 1985, 2:59-71.
Winkler et al., "Gene Transfer in Laboratory Fish: Model Organisms for the Analysis of Gene Function," Transgenic Animals, 1997, pp. 387-395.
Young et al., "Isolation of Embryonic Chick Myosatellite and Pluripotent Stem Cells," J. Tiss. Cult. Meth., Jun. 1992, 14(2):85-92, Springer Netherlands.
Coban, "Ischemia-Reperfusion Injury of Adipofascial Tissue: An Experimental Study Evaluating early Histologic and Biochemical Alterations in Rats," Mediators of Inflammation, 2005, 5, 304-308.
Liu, A. Y.-C., et al., "Transient Cold Shock Induces the Heat Shock Response upon Recovery at 37°C in Human Cells," J. Biol. Chem., May 20, 1994, 269(20), 14768-14775.
Nishikawa, "Ultrastructural Changes and Lipid Peroxidation in Rat Adipomusculocutaneous Flap Isotransplants after Normothermic Storage and Reperfusion," Transplantation,1992, 54, 795-801.
PCT International Search Report and Written Opinion for PCT/US2007/075935; Applicant: Zeltiq Aesthetics, Inc.; dated Apr. 10, 2008; 12 pgs.
Final Office Action; U.S. Appl. No. 10/391,221; Date of Mailing: Aug. 24, 2006, 4 pages.
Final Office Action; U.S. Appl. No. 11/016,196; Date of Mailing: Mar. 23, 2010, 12 pages.
Final Office Action; U.S. Appl. No. 11/435,502; Date of Mailing: Mar. 29, 2010, 11 pages.
International Search Report and Written Opinion for PCT/US2009/058088; Applicant: Zeltiq Aesthetics, Inc.; Date of Mailing: Nov. 20, 2009, 14 pages.
International Search Report and Written Opinion for PCT/US2009/067973; Applicant: Zeltiq Aesthetics, Inc.; Date of Mailing: Feb. 18, 2010, 10 pages.
Non-Final Office Action; U.S. Appl. No. 10/391,221; Date of Mailing: Jan. 25, 2006, 6 pages.
Non-Final Office Action; U.S. Appl. No. 10/391,221; Date of Mailing: May 30, 2007, 8 pages.
Non-Final Office Action; U.S. Appl. No. 10/391,221; Date of Mailing: Jul. 22, 2005, 6 pages.
Non-Final Office Action; U.S. Appl. No. 11/016,196; Date of Mailing: Apr. 22, 2008, 11 pages.
Non-Final Office Action; U.S. Appl. No. 11/016,196; Date of Mailing: Sep. 25, 2009, 8 pages.
Non-Final Office Action; U.S. Appl. No. 11/359,092; Date of Mailing: Nov. 19, 2009, 13 pages.
Non-Final Office Action; U.S. Appl. No. 11/528,225; Date of Mailing: Apr. 12, 2010, 11 pages.
Pre-Interview Office Action; U.S. Appl. No. 11/434,478; Date of Mailing: May 6, 2010, 4 pages.
European Search Report, European Patent Application No. 10167756.5, Applicant: The General Hospital Corporation, Mailing Date: Aug. 31, 2010, 6 pages.
European Search Report, European Patent Application No. EP07761461; Applicant: Zeltiq Aesthetics, Inc., Mailing Date: Apr. 25, 2012, 9 pages.
European Search Report, Supplement, European Patent Application No. EP08798416.7, Applicant: Zeltiq Aesthetics, Inc., Mailing Date: Jan. 12, 2012, 7 pages.
European Search Report, Supplement, European Patent Application No. EP09836823, Applicant: Zeltiq Aesthetics, Inc., Mailing Date: May 15, 2012, 5 pages.
Final Office Action; U.S. Appl. No. 11/528,225; Date of Mailing: Dec. 29, 2010, 9 pages.
Final Office Action; U.S. Appl. No. 11/558,046; Date of Mailing: Mar. 30, 2011, 17 pages.
Final Office Action; U.S. Appl. No. 11/741,271; Date of Mailing: Jul. 19, 2012, 8 pages.
Final Office Action; U.S. Appl. No. 11/750,953; Date of Mailing: Jul. 5, 2012, 11 pages.
International Search Report and Written Opinion for PCT/US2005/045988; Applicant: The General Hospital Corporation; Mailed on Apr. 25, 2006, 14 pages.
International Search Report and Written Opinion for PCT/US2010/033290; Applicant: Zeltiq Aesthetics, Inc.; Mailed on Feb. 25, 2011, 12 pages.
International Search Report and Written Opinion for PCT/US2011/022112; Applicant: Zeltiq Aesthetics, Inc.; Mailed on Mar. 18, 2011, 11 pages.
International Search Report and Written Opinion for PCT/US2011/022444; Applicant: Zeltiq Aesthetics, Inc., Mailed on Mar. 29, 2011, 14 pages.
International Search Report and Written Opinion for PCT/US2012/022585; Mailed on May 18, 2012, 14 pages.
Merrill, Tom, "A Chill to the Heart: A System to Deliver Local Hypothermia Could One Day Improve the Lives of Heart-Attack Patients," Mechanical Engineering Magazine, Oct. 2010 (10 pages).
Non-Final Office Action; U.S. Appl. No. 11/528,189; Date of Mailing Apr. 6, 2012, 9 pages.

Non-Final Office Action; U.S. Appl. No. 11/528,225; Date of Mailing: Aug. 3, 2011, 11 pages.

Non-Final Office Action; U.S. Appl. No. 11/558,046; Date of Mailing: Jul. 12, 2010, 14 pages.

Non-Final Office Action; U.S. Appl. No. 11/741,271; Date of Mailing: Jul. 12, 2010, 9 pages.

Non-Final Office Action; U.S. Appl. No. 12/337,544; Date of Mailing: Mar. 30, 2012, 13 pgs.

Non-Final Office Action; U.S. Appl. No. 12/565,613; Date of Mailing: Sep. 23, 2011, 32 pages.

Non-Final Office Action; U.S. Appl. No. 12/942,852; Date of Mailing: Mar. 7, 2011, 6 pages.

Non-Final Office Action; U.S. Appl. No. 12/942,852; Date of Mailing: Jun. 30, 2011, 10 pages.

Wang et al., "Cryopreservation of cell/hydrogel constructs based on a new cell-assembling technique", Sep. 5, 2009, 40 pages.

Wharton et al., "Cold acclimation and cryoprotectants in a freeze-tolerant Antarctic nematode, *Panagrolaimus davidi*," Mar. 7, 2000, 2 pages.

European Search Report; Application No. EP10770461; Dated Aug. 31, 2012; Applicant: Zeltiq Aesthetics, Inc. 5 pgs.

Non-Final Office Action; U.S. Appl. No. 12/840,235; Date of Mailing: Apr. 11, 2013; 9 pages.

Notice of Publication; U.S. Appl. No. 13/616,633; Date of Mailing: Mar. 28, 2013; 1 page.

SYSTEM FOR TREATING LIPID-RICH REGIONS

BACKGROUND

Excess body fat, or adipose tissue, may be present in various locations of the body, including, for example, the thigh, buttocks, abdomen, knees, back, face, arms, and other areas. Excess adipose tissue can detract from personal appearance and athletic performance. Moreover, excess adipose tissue is thought to magnify the unattractive appearance of cellulite, which forms when subcutaneous fat protrudes into the dermis and creates dimples where the skin is attached to underlying structural fibrous strands. Cellulite and excessive amounts of adipose tissue are often considered to be unappealing. Moreover, significant health risks may be associated with higher amounts of excess body fat. An effective way of controlling or removing excess body fat therefore is needed.

Liposuction is a method for selectively removing adipose tissue to "sculpt" a person's body. Liposuction typically is performed by plastic surgeons or dermatologists using specialized surgical equipment that invasively removes subcutaneous adipose tissue via suction. One drawback of liposuction is that it is a surgical procedure, and the recovery may be painful and lengthy. Moreover, the procedure typically requires the injection of tumescent anesthetics, which is often associated with temporary bruising. Liposuction can also have serious and occasionally even fatal complications. In addition, the cost for liposuction is usually substantial. Other emerging techniques for removal of subcutaneous adipose tissue include mesotherapy, laser-assisted liposuction, and high intensity focused ultrasound.

Conventional non-invasive treatments for removing excess body fat typically include topical agents, weight-loss drugs, regular exercise, dieting, or a combination of these treatments. One drawback of these treatments is that they may not be effective or even possible under certain circumstances. For example, when a person is physically injured or ill, regular exercise may not be an option. Similarly, weight-loss drugs or topical agents are not an option when they cause an allergic or negative reaction. Furthermore, fat loss in selective areas of a person's body cannot be achieved using general or systemic weight-loss methods.

Other non-invasive treatment methods include applying heat to a zone of subcutaneous lipid-rich cells. U.S. Pat. No. 5,948,011 discloses altering subcutaneous body fat and/or collagen by heating the subcutaneous fat layer with radiant energy while cooling the surface of the skin. The applied heat denatures fibrous septae made of collagen tissue and may destroy fat cells below the skin, and the cooling protects the epidermis from thermal damage. This method is less invasive than liposuction, but it still may cause thermal damage to adjacent tissue, and can also be painful and unpredictable.

Additional methods and devices to reduce subcutaneous adipose tissue are disclosed in U.S. Patent Publication Nos. 2003/0220674 and 2005/0251120, the entire disclosures of which are incorporated herein. Although the methods and devices disclosed in these publications are promising, several improvements for enhancing the implementation of these methods and devices would be desirable.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

DETAILED DESCRIPTION

A. Overview

Figure 1:
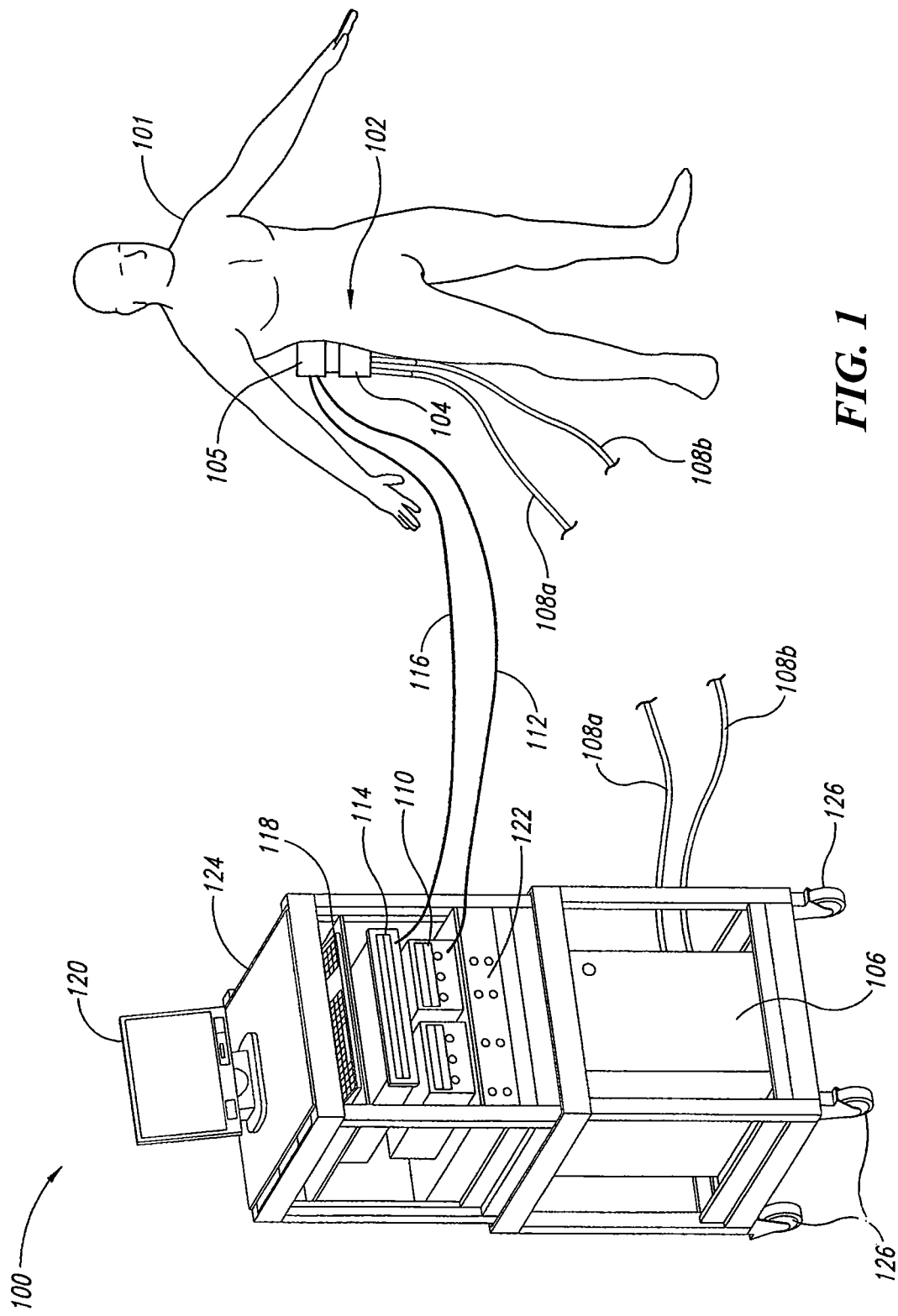
FIG. 1 is an isometric view of an embodiment of a system for treating subcutaneous lipid-rich regions of a subject.

A system is described for treating a subject's subcutaneous adipose tissue, such as by cooling. The term "subcutaneous tissue" means tissue lying beneath the dermis and includes subcutaneous fat, or adipose tissue, which primarily is composed of lipid-rich cells, or adipocytes. In various embodiments, the system includes a controller, a computing device, a data acquisition device, a chiller, and one or more applicators. The system can employ these components in various embodiments to receive a selection of a treatment profile and apply the selected treatment using an applicator.

An applicator is a component of the system that cools a region of a subject, such as a human or animal. Various types of applicators may be applied during treatment, such as a massage or vibrating applicator, a vacuum applicator, a belt applicator, and so forth. Each applicator may be designed to treat identified portions of the subject's body, such as chin, cheeks, arms, pectoral areas, thighs, calves, buttocks, and so forth. As an example, the massage or vibrating applicator may be applied at the pectoral region, the vacuum applicator may be applied at the cheek region, and the belt applicator can be applied around the thigh region. One type of applicator is described in commonly assigned U.S. patent application Ser. No. 11/528,189, entitled "COOLING DEVICES WITH FLEXIBLE SENSORS," which was filed on Sep. 26, 2006, and is incorporated herein in its entirety by reference.

A patient protection device is an apparatus that prevents the applicator from directly contacting a subject's skin and thereby can reduce the likelihood of cross-infection between subjects and minimize cleaning requirements for the applicator. The patient protection device may be reused or may be configured to enforce single use electrically, mechanically, electromechanically, or any combination thereof. The patient protection device may include or incorporate a sterility barrier, various electronics, sensors, memory, and/or security components. A patient protection device can be implemented as a sleeve (e.g., a disposable sleeve), a plate, a sheet, or any other surface. The patient protection device may also include or incorporate various storage and communications devices, such as a radio frequency identification (RFID) component. A patient protection device may specifically be designed for use with a limited set of applicators. When the patient protection device is applied to an applicator, memory associated with it may be accessible by a controller that controls aspects of the system. The memory can include one or more treatment profiles. Each treatment profile can include one or more segments, and each segment can include a specified duration, a target temperature, and control parameters for features such as vibration, massage, vacuum, and other treatment modes. Upon receiving input to start the treatment, the controller can cause the applicator to cycle through each segment of the treatment profile. In so doing, the applicator applies power to one or more cooling devices, such as thermoelectric coolers, to begin a cooling cycle and, for example, activate features or modes such as vibration, massage, vacuum, etc. Using temperature sensors proximate to the one or more cooling devices, the patient's skin, or other locations, the controller determines whether a temperature that is sufficiently close to the target temperature has been reached. Although the remainder of this detailed discussion and the appended claims may describe or imply that a region of the body (e.g., adipose tissue) has been cooled or heated to the target temperature, in actuality that region of the body may be close but not equal to the target temperature, e.g., because of the body's natural heating and cooling variations. Thus, although the system may attempt to heat or cool to the target temperature, a sensor may measure a sufficiently close temperature. If the target temperature has not been reached, power may be increased or decreased, as needed, to maintain the target temperature or "set-point." When the indicated duration expires, the controller may apply the temperature and duration indicated in the next treatment profile segment. In some embodiments, temperature can be controlled using a variable other than, or in addition to, power.

When the controller controls the temperature applied by the applicator, it may employ a chiller. A chiller is a device that, based on variable power input, can increase or decrease the temperature at a connected cooling device that in turn may be attached to or incorporated into the applicator. As previously described, the applicator can have one or more attached cooling devices, such as thermoelectric coolers. The chillers can employ a number of cooling technologies including, for example, thermoelectric coolers, recirculating chilled fluid, vapor compression elements, or phase change cryogenic devices. One skilled in the art will recognize that there are a number of other cooling technologies that could be used such that the chillers need not be limited to those described herein.

A data acquisition device component of the system can collect data from the controller, chiller, applicator, and other components. As examples, the data acquisition device can collect information such as how much power is being applied to cooling devices, the temperature at each cooling device, the temperature at the subject's skin, the status of the chiller, controller, or applicator, and so forth. The data acquisition device component can provide the collected information to a computing device.

The computing device can receive the information the data acquisition device component collects, collect other information, such as from the patient protection device or from user input, and take various actions, such as by commanding the controller. As an example, the computing device can cause the controller to increase or decrease the temperature at various cooling devices based on the indicated skin temperature, selected treatment profile, and so forth.

The computing device or the applicator can provide various user interfaces, such as to begin treatment; display treatment profiles or their segments, current status, or terminate treatment; provide alarms or other notifications relating to abnormal or unexpected conditions; and so forth. These user interfaces can be provided to operators of the system or to subjects. The system will now be described with reference to the Figures.

B. System Components

FIG. 1 is an isometric view of an embodiment of a system 100 for removing heat from subcutaneous lipid-rich regions of a subject 101. The system 100 can include a cooling device 104 including an applicator 105; the cooling device 104 can be placed at an abdominal area 102 of the subject 101 or at any another suitable area for removing heat from a subcutaneous lipid-rich region of the subject 101. Various shapes and sizes of cooling devices 104 and applicators 105 can be applied to different regions.

The system 100 can further include a chiller 106 and supply and return fluid lines 108a-b between the cooling device 104 and the chiller 106. The chiller 106 can remove heat from a circulating coolant to a heat sink and provide a chilled coolant to the cooling device 104 via the fluid lines 108a-b. Examples of the circulating coolant include water, glycol, synthetic heat transfer fluid, oil, a refrigerant, and/or any other suitable heat conducting fluid. The fluid lines 108a-b can be hoses or other conduits constructed from polyethylene, polyvinyl chloride, polyurethane, and/or other materials that can accommodate the particular circulating coolant. The chiller 106 can be a refrigeration unit, a cooling tower, a thermoelectric chiller, or any other device capable of removing heat from a coolant.

As previously explained, a cooling device 104 can include one or more heat exchanging units. The heat exchanging unit can be a Peltier-type thermoelectric element, and the cooling device 104 can have multiple individually controlled heat exchanging units to create a custom spatial cooling profile. The system 100 can further include a power supply 110 and a controller 114 operatively coupled to the cooling device 104 and the applicator 105. In one embodiment, the power supply 110 can provide a direct current voltage to the thermoelectric cooling device 104 and/or the applicator 105 to remove heat from the subject 101. The controller 114 can monitor process parameters via sensors (not shown) placed proximate to the cooling device 104 via a control line 116 to adjust the heat removal rate based on the process parameters. The controller 114 can further monitor process parameters to adjust the applicator 105 based on treatment parameters, such as treatment parameters defined in a treatment profile. The controller 114 can exchange data with the applicator via a line 112 or via wireless communication. The controller 114 can include any processor, Programmable Logic Controller, Distributed Control System, secure processor, and the like. A secure processor can be implemented as an integrated circuit with access-controlled physical interfaces; tamper resistant containment; means of detecting and responding to physical tampering; secure storage; and shielded execution of computer-executable instructions. Some secure processors also provide cryptographic accelerator circuitry. Secure storage may also be implemented as a secure flash memory, secure serial EEPROM, secure field programmable gate array, or secure application-specific integrated circuit.

In another aspect, the controller 114 can receive data from an input device 118, transmit data to an output device 120, and/or exchange data with a control panel 122. The input device 118 can include a keyboard, a mouse, a stylus, a touch screen, a push button, a switch, a potentiometer, a scanner, or any other device suitable for accepting user input. The output device 120 can include a display screen, a printer, a medium reader, an audio device, or any other device suitable for providing user feedback. The control panel 122 can include indicator lights, numerical displays, and audio devices. In alternative embodiments, the cooling device 104 can include the input device 118, output device 120, and/or control panel 122. In embodiments FIG. 1 illustrates, the controller 114, power supply 110, control panel 122, chiller 106, input device 118, and output device 120 can be carried by a rack 124 with wheels 126 for portability. In alternative embodiments, the controller 114 can be contained on the cooling device 104 or on the applicator 105. In other embodiments, the various components can be fixedly installed at a treatment site.

Although a noninvasive applicator is illustrated and discussed herein, minimally invasive applicators may also be employed. In such a case, the applicator and patient protection device may be integrated. As an example, a cryoprobe that may be inserted directly into the subcutaneous adipose tissue to cool or freeze the tissue is an example of such a minimally invasive applicator. Cryoprobes manufactured by, e.g., Endocare, Inc., of Irvine, Calif. are suitable for such applications. This patent application incorporates by reference U.S. Pat. No. 6,494,844, entitled "DEVICE FOR BIOPSY AND TREATMENT OF BREAST TUMORS"; U.S. Pat. No. 6,551,255, entitled "DEVICE FOR BIOPSY OF TUMORS"; U.S. Publication No. 2007-0055173, entitled "ROTATIONAL CORE BIOPSY DEVICE WITH LIQUID CRYOGEN ADHESION PROBE"; U.S. Pat. No. 6,789,545, entitled "METHOD AND SYSTEM FOR CRYOABLATING FIBROADENOMAS"; U.S. Publication No. 2004-0215294, entitled "CRYOTHERAPY PROBE"; U.S. Pat. No. 7,083,612, entitled "CRYOTHERAPY SYSTEM"; and U.S. Publication No. 2005-0261753, entitled "METHODS AND SYSTEMS FOR CRYOGENIC COOLING".

Figure 2:
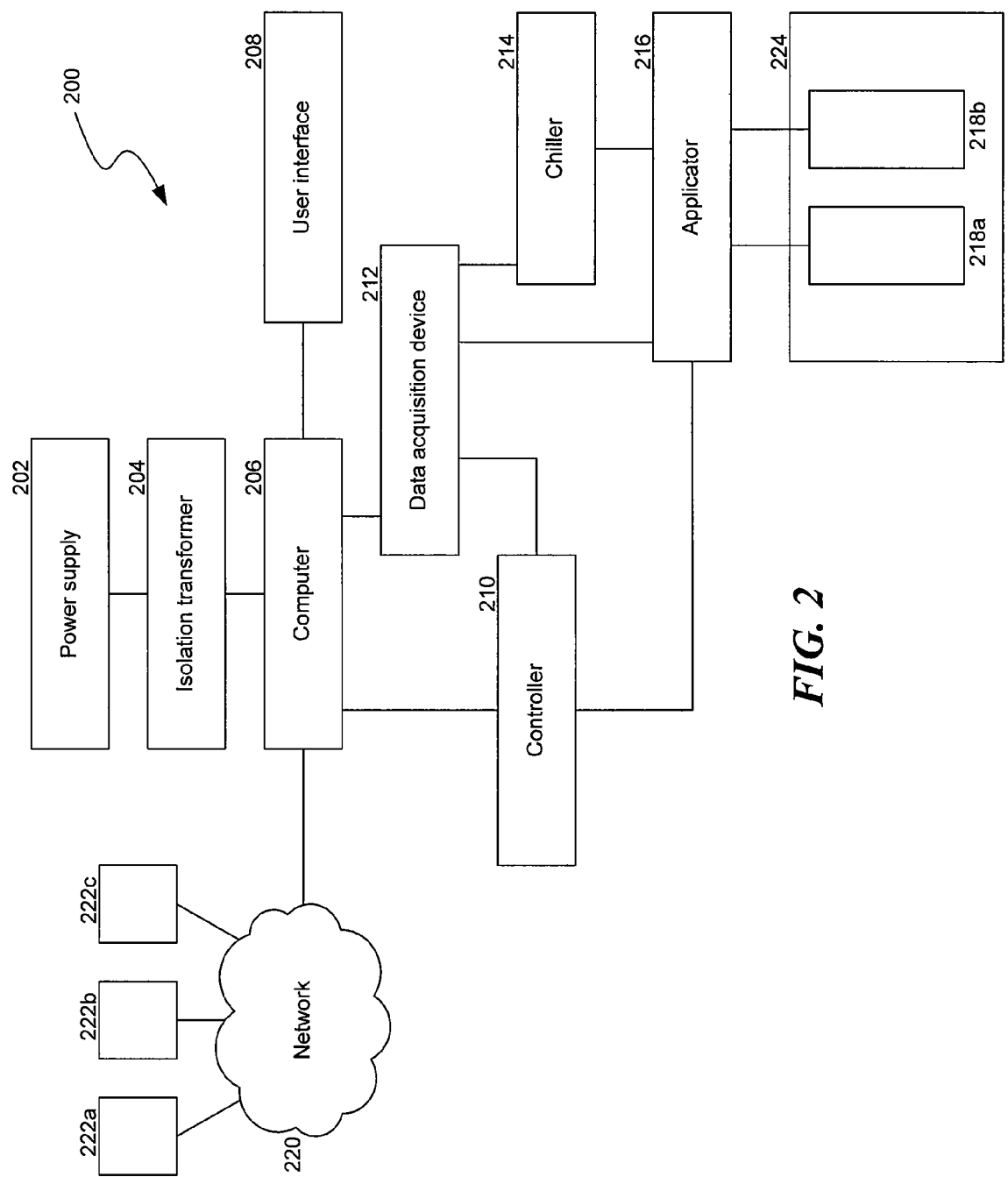
FIG. 2 is a block diagram illustrating an environment in which the system may operate in some embodiments.

FIG. 2 is a block diagram illustrating an environment in which the system may operate in some embodiments. The environment 200 includes a power supply 202 and an isolation transformer 204. The power supply 202 can be any ordinary type of power supply, such as alternating current or direct current. The isolation transformer 204 can be a medical grade transformer that isolates the subject from power fluctuations and problems, such as leakage current, voltage spikes or dips, and so forth. The environment 200 also includes a computing device 206 and a user interface 208. The computing device 206 can be integrated with a controller 210 or can be a separate unit. As an example, the computing device 206 can be a single board computer that is adapted for use within a housing of the controller 210. In some embodiments, the controller 210 can be integrated with an applicator 216.

The user interface 208 can include various input devices for collecting input from a user, such as an operator of the system, and can also include various output devices, such as for providing information to the operator, subject, and so forth. The computing device can be connected to the controller to receive input from the controller and provide commands to the controller. Various components of the system may connect to other components via wired or wireless connections, such as Ethernet, serial (e.g., RS-232 or universal serial bus) connections, parallel connections, IEEE 802.11, IEEE 802.15, IEEE 802.16, "WiMAX," IEEE 1394, infrared, Bluetooth, and so forth.

The computing device can also connect to a data acquisition device 212. The data acquisition device 212 can acquire data from various components, such as the controller 210, a chiller 214, and an applicator 216, and provide the retrieved data to other components, such as to the computing device 206. In various embodiments, the data acquisition device can be incorporated into the controller or applicator.

The computing device 206 can employ the data it receives from the data acquisition device 212, such as to command the controller 210 to take various actions. As an example, the computing device 206 may command the controller 210 to change operating parameters at the applicator. As another example, detecting that the skin temperature of the subject is too low, the computing device 206 can cause the applicator 216 to increase the temperature via the controller 210. Other connections between components may also exist in various embodiments, but are not illustrated. As an example, the controller 210 can connect to the chiller 214, such as to command the chiller. Alternatively, the connections can be indirect. As an example, the controller 210 can command the chiller 214 via the applicator 216. The applicator can connect to one or more heat exchanging units 218a and 218b, such as thermoelectric heat exchanging units. The heat exchanging units 218a-b may be housed in a patient protection device 224. In some embodiments, the applicator 216 and heat exchanging units 218a-b may together be housed in a patient protection device 224.

The applicator 216 or associated cooling device can include thermoelectric heat exchanging units, heat exchanging unit temperature sensors, chemical sensors, electrical sensors, moisture sensors, skin temperature sensors, vacuum devices, and vibration or massage devices. The applicator can receive commands from a controller 210 to control temperature, vacuum, vibration, and so forth. It may also provide temperature or operating information to the controller 210 or computing device 206, such as via the data acquisition device 212.

In some embodiments, the patient protection device 224 can be disposed of and replaced in any manner and interval as desired, such as after every use, with each new subject, after a selected time period or number of uses, and so forth. Information on the application of a patient protection device to a patient or subject can be stored in a memory associated with the patient protection device. In various embodiments, various components of the system, such as patient protection devices, can employ a secure processor, smart cards, secure memory, or any combination thereof. Secure processors include smartcard devices produced by Renesas Technology Corp., of Tokyo, Japan, that enable memory access through dynamic symmetric mutual authentication, data encryption, and other software-based or firmware-based security techniques. The contents of this memory cannot be accessed by devices or software that do not conform to the security measures. Moreover, the secure processor may employ tamper detection circuitry to also prevent hardware attacks. These and other security measures may be implemented to ensure subject safety or privacy concerns, comply with laws or regulations, and to generally ensure safety and integrity of the system. In some embodiments, the secure processor can be connected to flex circuits. A flex circuit is a printed circuit board that is pliable and that may be integrated with some types of applicators or patient protection devices, such as patient protection device 224.

Some components may also employ secure enclosures in various embodiments. As an example, the controller 210 and/or computing device 206 can be housed in a secure enclosure. The secure enclosure may include features to deter physical access to the components of the system, such as switches to detect intrusion. The controller 210 and/or computing device 206 can include hardware and firmware to respond to detected intrusions, such as by disabling the ability to perform treatments, erasing memory, and so forth.

The computing device 206 may connect to network resources, such as other computers 222a-c. As examples, the computing device 206 may connect to a server 222a to upload data logs, subject information, use information, and so forth. The computing device 206 may also connect to a server 222b to download updates to software, lists of applicators or patient protection devices that should be disabled, and so forth. As an example, once a patient protection device 224 has passed its expiry date or its lifespan has otherwise been determined to be expired, the computing device 206 may upload an identifier associated with the patient protection device to a server for download by other computing devices so that the expired patient protection device cannot be used with other systems. The computing device 206 may connect to network resources via a network 220, such as the Internet or an intranet.

Figure 3:
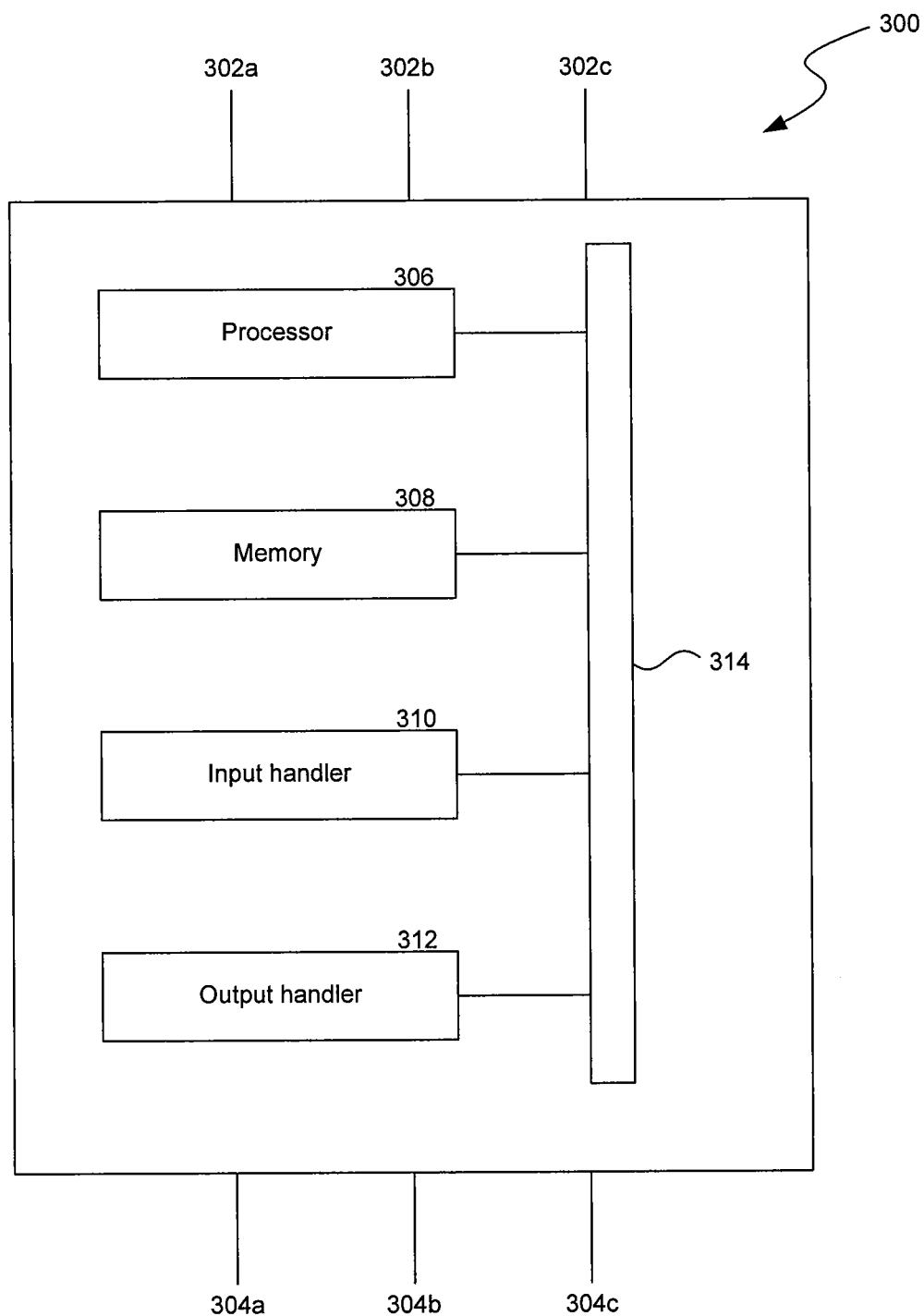
FIG. 3 is a block diagram illustrating subcomponents of components of the system in various embodiments.

FIG. 3 is a block diagram illustrating subcomponents of components of the cooling facility in various embodiments. Components of the cooling facility, such as the computing device 206, controller 210, data acquisition device 212, applicator 216, or patient protection device 224, can include a computing environment 300. The computing environment 300 can include input lines 302a, 302b, and 302c. In various embodiments, multiple input lines may be employed. The computing environment 300 can also provide output lines 304a, 304b, and 304c. In various embodiments, multiple output lines may be provided. The computing environment may also include a processor 306, memory 308, input handler 310, output handler 312, and bus 314.

In various embodiments, the processor 306 can be a standard central processing unit or a secure processor. Secure processors can be special-purpose processors (e.g., reduced instruction set processor) that can withstand sophisticated attacks that attempt to extract data or programming logic. The secure processors may not have debugging pins that enable an external debugger to monitor the secure processor's execution or registers. In other embodiments, the system may employ a secure field programmable gate array, a smartcard, or other secure devices. Smartcards are defined by ISO 7816, the specification for which is incorporated herein in its entirety by reference.

The memory 308 can be standard memory, secure memory, or a combination of both memory types. By employing a secure processor and/or secure memory, the system can ensure that data and instructions are both highly secure and sensitive operations such as decryption are shielded from observation.

The input handler 310 and output handler 312 retrieve input from lines 302a-c and provide output to lines 304a-c, such as via the bus 314.

In various embodiments, the system employs secure processors and/or secure memory in connection with the controller applicator, and patient protection device, in any combination. Any secure processor of one component can verify another component, such as by issuing a challenge to the other component and verifying a response to the challenge received from a secure processor of the other component. Such a challenge/response system using secure processors is described, for example, in U.S. Pat. No. 7,096,204, to Chen et al., which is incorporated herein in its entirety by reference.

C. System Data Structures

In various embodiments, the system can employ data structures that are stored in memory, such as in memory associated with secure processors ("secure processor memory") or in secure memory. The data structures enable the system to provide treatment choices, ensure system integrity, and protect subject safety and privacy.

While the table data structures discussed below illustrate data structures with contents and organization that are designed to make them more comprehensible by a human reader, those skilled in the art will appreciate that actual data structures used by the facility to store this information may differ from the illustrated data structures, in that they, for example, may be organized in a different manner, may contain more or less information than shown, may be compressed and/or encrypted; etc.

Figure 4:
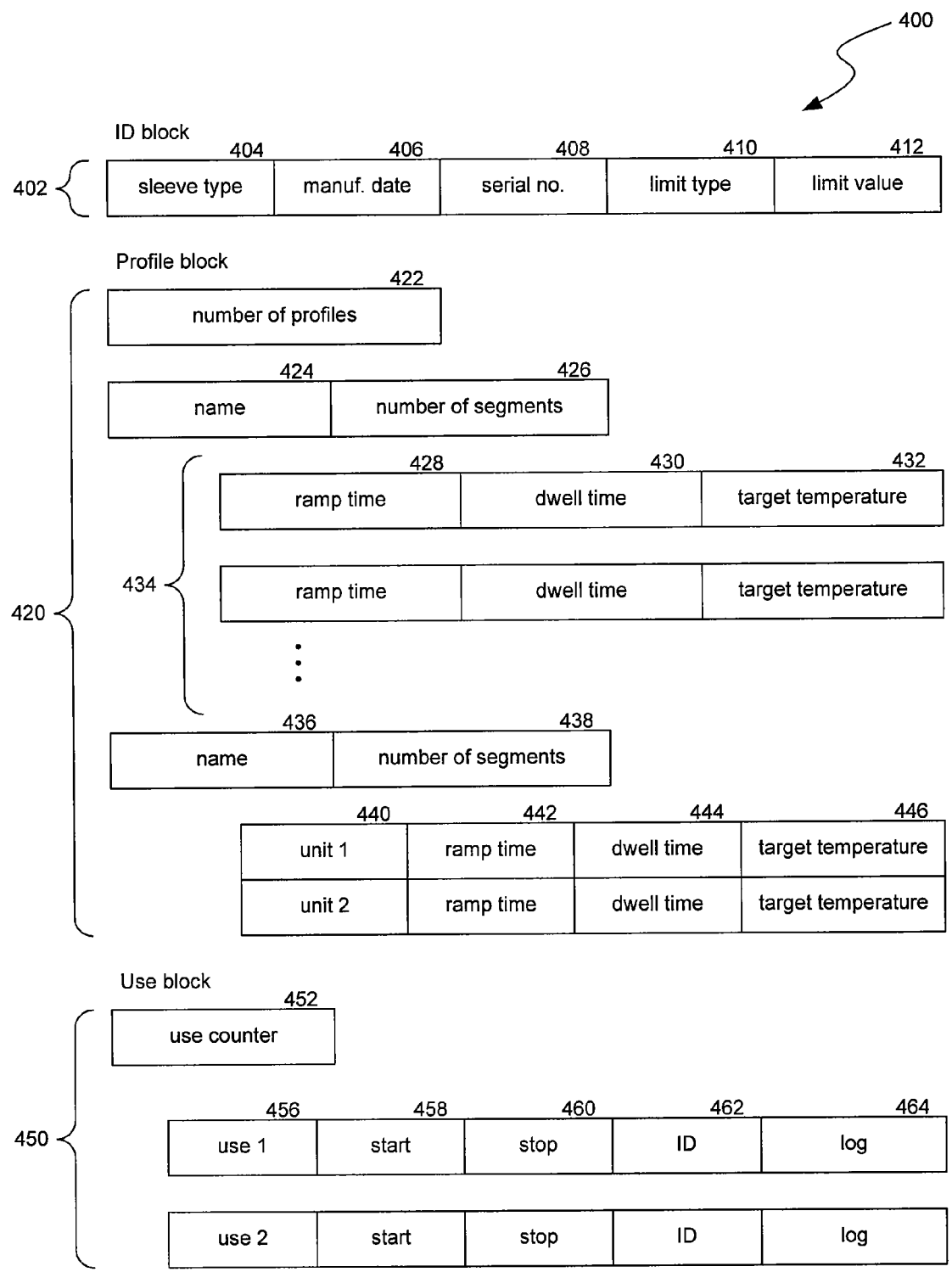
FIG. 4 is a block diagram illustrating data structures employed by the system in various embodiments.

FIG. 4 is a block diagram illustrating data structures employed by the system in various embodiments. The illustrated data structures 400 can be stored in memory associated with various components of the system, such as secure processor memory or secure memory associated with patient protection devices. Some of the data structures 400 may be indicated for read-only access, write-only access, or read/write access. The type of access can be enforced via a combination of hardware and/or software. As an example, when a field of the data structure is marked for read-only access, various algorithms associated with the system may not attempt to write to the field. Moreover, the memory device storing the data structure may also prevent the field from being written to. When a field is marked for read-only access, the field may nevertheless be writable before it is deployed, such as by the manufacturer or distributor. As an example, a special encryption key or authentication key may be employed to write to read-only data structure fields.

The data structures 400 can include an identifier ("ID") block 402, profiles block 420, and use block 450. Each of these blocks will now be described.

The ID block 402 can include fields for a patient protection device type 404, manufacturing date 406, serial number 408, and one or more limit type 410, limit value 412 pairs. These fields are generally indicated for read-only access. The patient protection device type field 404 can store the type of patient protection device, such as whether or not the patient protection device is disposable, the types of applicators the patient protection device is compatible with, the manufacturer of the patient protection device, and so forth. The manufacturing date field 406 can store the date on which the patient protection device was manufactured or distributed. The serial number field 408 can store a unique patient protection device identifier.

The limit type field 410 stores the type of limit that is imposed on the patient protection device. Limit types can include use counts, dates, times, and so forth. The system includes flexibility in defining limit types. As an example, one patient protection device type may have use-based limits whereas another patient protection device type may have time-based limits, and a third patient protection device type may include both time- and use-based limits. When the limit is based on use, the limit value field 412 may store the number of times that the corresponding patient protection device can be used. As an example, when the value stored by the limit type field 410 indicates that the limit is based on use, the limit value field 412 may indicate that the patient protection device expires after one use. When the limit is based on dates or times, the limit value field 412 may store the date or time duration after which the patient protection device expires. As an example, when the value stored by the limit type field 410 indicates that the limit is based on date, the limit value field 412 may store a specific date after which the patient protection device cannot be used, such as the date at which the shelf life of a sterile patient protection device expires. As another example, when the value stored by the limit type field 410 indicates that the limit is based on a time duration, the limit value field 412 may store a time duration after which the patient protection device cannot be used. The time duration may be measured from the time the patient protection device is first used.

The profiles block 420 stores information pertaining to treatment profiles. This includes a number of profiles field 422 for storing the number of profiles that are stored in the profiles block. Each profile indicates a name and has a number of segments, which are identified in the profiles block, such as in fields 424, 426, 436, and 438. Each profile also provides treatment-related information for each segment. As an example, segments 434 provide treatment-related information associated to the first profile identified in the illustrated profiles block. The treatment-related information may include information such as ramp time 428, dwell time 430, and target temperature 432. The ramp time is the amount of time, such as in seconds, that the system is to take to cool (or heat) a heat exchanging unit associated with an applicator so as to arrive at the target temperature 432 at the end of the specified amount of time. Various curves can be used to change the temperature, such as linear, asymptotic, geometric, and so forth. The dwell time 430 indicates the amount of time, such as in seconds, that the heat exchanging unit is to apply the target temperature 432. Other information may be used in segments 434 in various combinations to effect a particular desired treatment profile. The number of segments for each profile is stored in the number of segments fields associated with each profile, such as fields 426 and 438. The name fields 424 and 436 can store names associated with each profile. These names can be retrieved and displayed in a user interface that an operator of the system can use to select a profile. Each segment of a profile can identify parameters for one or more heat exchanging units associated with an applicator. As an example, blocks 440-446 identify parameters that can be used to control heat exchanging units independently. Thus, for example, when an applicator with multiple heat exchanging units is employed, different areas of the subject's body proximate to each heat exchanging unit can receive different cooling treatments. The profiles block may also include additional fields, such as to indicate whether a vacuum device, vibrator device, or massage device should be turned on or off, the vacuum force or vibration frequency, and so forth. The profiles block 420 may also be indicated for read-only access.

The use block 450 stores information relating to use of a component, such as use of the patient protection device associated with the memory storing the use block 450. The use block 450 can include a use counter field 452, a use identifier field 456, a use start time field 458, a use stop time field 460, an identifier ("ID") field 462, and a log field 464. The use counter field 452 stores a count of the number of times the patient protection device has been used during application of a treatment. A record can be stored in the use block for each use. The use identifier field 456 identifies the record. The use start time field 458 stores the time at which treatment started and the use stop time field 460 stores the time at which treatment stopped. The ID field 462 stores an identifier, such as an identifier of the applicator and/or controller component that was used during treatment, a patient identifier, and so forth. The log field 464 stores a log of operational characteristics, such as errors, profiles applied, and information from various sensors, such as temperature sensors. In various embodiments, the system may transmit information contained in the use block, such as to a distributor or manufacturer for tracking or troubleshooting purposes. Fields in the use block can be indicated for read/write access.

In various embodiments, additional data structures can be added, such as to store calibration data, diagnostic data, test data, security data (e.g., to store security keys), executable code, and so forth.

D. System Routines

The system invokes a number of routines. While some of the routines are described herein, one skilled in the art is capable of identifying other routines the system could perform. Moreover, the routines described herein can be altered in various ways. As examples, the order of illustrated logic may be rearranged, substeps may be performed in parallel, illustrated logic may be omitted, other logic may be included, etc.

Figure 5:
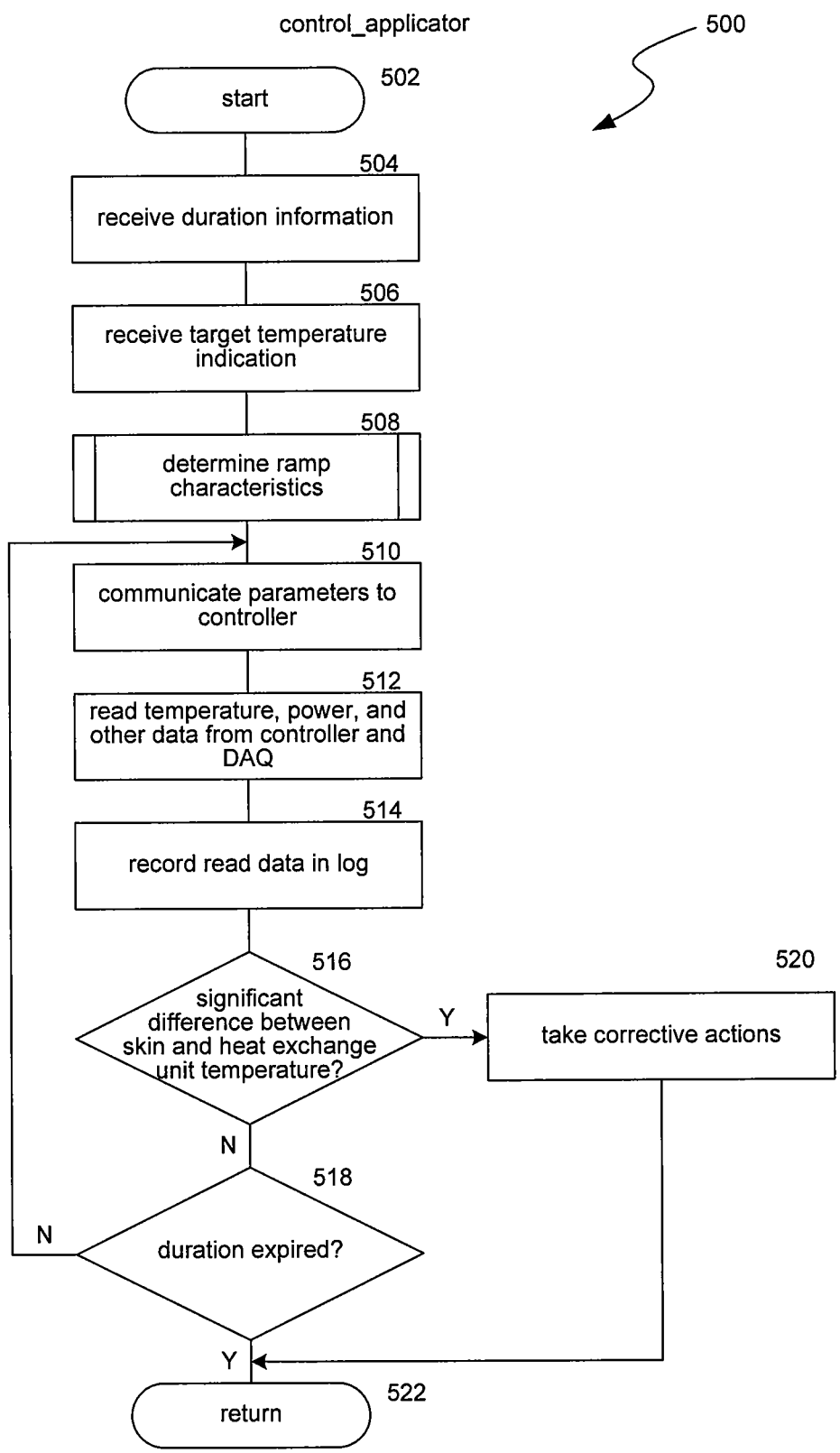
FIG. 5 is a flow diagram illustrating a control_applicator routine invoked by the system in some embodiments.

FIG. 5 is a flow diagram illustrating a control_applicator routine invoked by the system in some embodiments. The routine can be invoked by a computing device, such as a single board computer associated with a controller, to control an applicator. As an example, the computing device may invoke the control applicator routine 500 after an operator selects a treatment profile from a list of treatment profiles. The routine 500 begins at block 502.

At block 504, the routine receives duration information, such as ramp time and dwell time. This information can be retrieved from a selected treatment profile. At block 506, the routine receives a target temperature indication. The target temperature is the temperature identified in the first segment of the selected treatment profile.

Within the loop delimited by blocks 508 and 518, the routine causes the applicator to cycle through each segment of the selected treatment profile. At block 508, the routine determines ramp characteristics. Ramp characteristics determine the slope of the increase or decrease in temperature as a function of time. Ramp characteristics can be implemented using various control schemes, such as open loop, bang-bang overshoot, proportional, proportional integral, proportional integral derivative, and others. In the open loop ramp control scheme, the system sends a constant amount of power and does not adjust power based on temperature feedback from sensors. In the bang-bang overshoot control scheme, the system applies power, and when it senses via a temperature sensor that it has passed the target temperature, it applies more or less cooling, as appropriate. As an example, when thermoelectric coolers are used, greater power can lead to lower temperatures, so the heat exchanging unit may increase power to cause additional cooling. In the proportional control scheme, the system compares the target temperature with the actual temperature (e.g., at the applicator) and applies a transfer function (e.g., to the power) to correct the temperature. The transfer function can be proportional to the amount of difference between the target and actual temperatures. In the proportional integral control scheme, prior differences between the target and actual temperatures are additionally incorporated when attempting to achieve the target temperature. In the proportional integral derivative control scheme, the first derivative of the prior differences is used to reduce the possibility of overshooting the target temperature and react to system perturbations in a more stable manner.

At block 510, the routine communicates parameters, such as ramp time, dwell time, target temperature, and ramp characteristics, to the controller so that the controller can effectuate the segment of the treatment profile that is presently being applied. At block 512, the routine reads temperature, power, and other data from the controller and/or the data acquisition device ("DAQ"). At block 514, the routine records the read data in a log, such as in a log that is stored in memory or a database. The data that is stored in the log can be transmitted, such as to a server or other computing device via a network or other connection.

At decision block 516, the routine determines whether there is a significant difference between the temperatures of the subject's skin and one or more heat exchanging units associated with the controlled applicator. In various embodiments, the significance of the temperature difference can be specified by an operator, by a treatment profile, and so forth. The temperature difference can also be tuned, such as based on the sensitivity of the subject. If the temperature difference is significant, the routine continues at block 520. Otherwise, the routine continues at decision block 518. At block 520, the routine takes corrective actions. As an example, the routine may cause the applicator to raise the temperature of the heat exchanging units having a significant temperature difference, alert the operator to the condition, terminate the treatment, and so forth. The routine may then continue at block 522, where it returns.

At decision block 518, the routine determines whether the duration, e.g., the dwell time, has expired. If the duration has expired, the routine continues at block 522, where it returns. Otherwise, the routine continues at block 510. In various embodiments, the routine may be invoked for each segment of a treatment profile.

The system can update various data structures when a treatment is applied. The updates can occur before treatment begins or after it ends. These updates can include use counts, treatment profiles applied, and times treatment started or stopped. The updates can also include records of treatment attributes, such as temperatures, error conditions, and so forth. The updates can be made in secure processors or other secure memory associated with, e.g., patient protection devices, controllers, applicators, computing devices, or other components.

Figure 6:
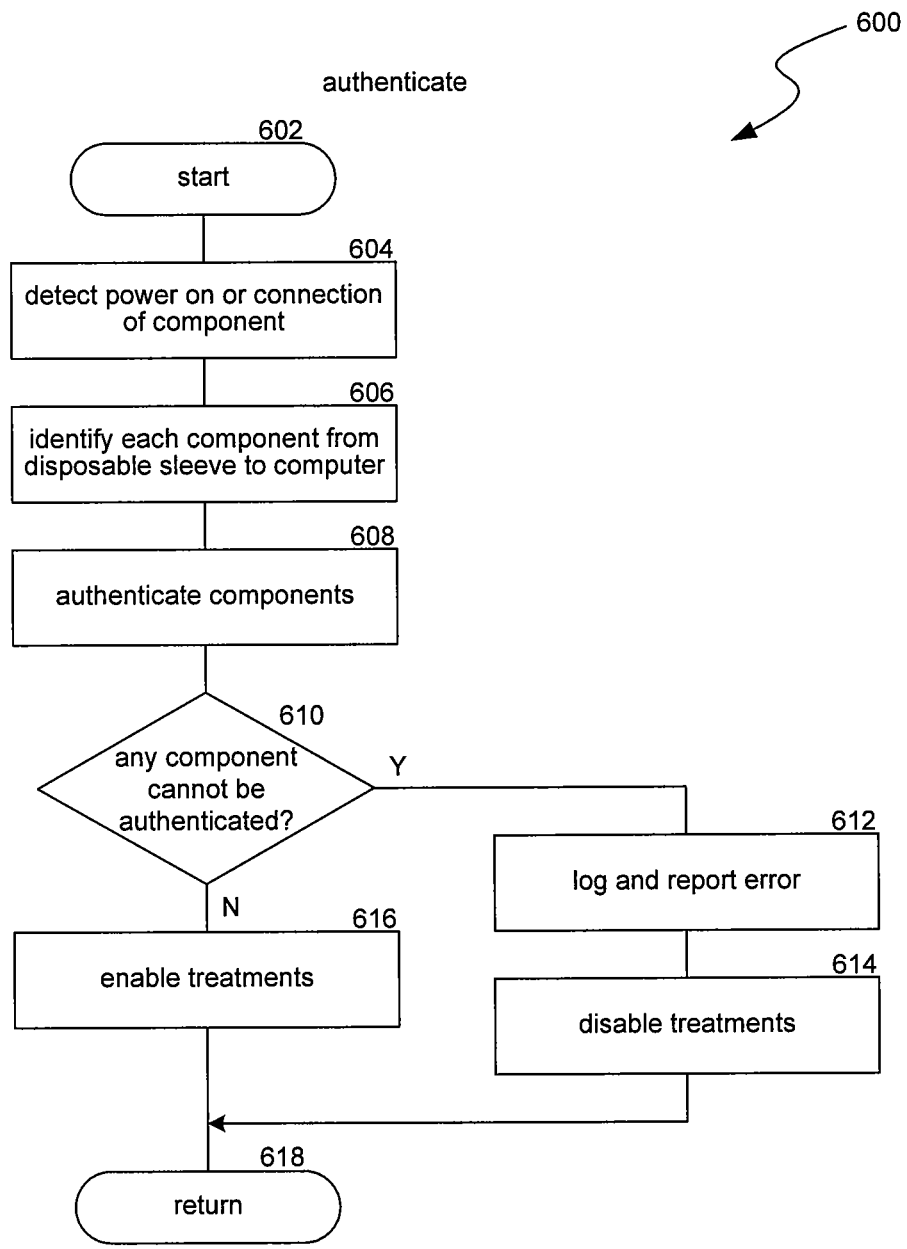
FIG. 6 is a flow diagram illustrating an authenticate routine invoked by the system in some embodiments.

FIG. 6 is a flow diagram illustrating an authenticate routine invoked by the system in some embodiments. The system can invoke the authenticate routine 600 when it powers on or when it detects that a component has connected to the system. As an example, the system may invoke the authenticate routine 600 when a patient protection device is connected to the system. The routine 600 authenticates each component that is connected to the system. The routine 600 begins at block 602.

At block 604, the routine detects a power on condition or connection of a component. The system may invoke the routine 600 when an applicator, patient protection device, or other component is connected to the system.

At block 606, the routine identifies each component that is connected to the system, spanning the entire chain from the patient protection device to the computing device that executes the routine. In various embodiments, the routine may identify all components in the chain even though the component that invokes the routine may be within the chain or not even in the chain.

At block 608, the routine authenticates all components in the chain of components. In various embodiments, the routine may authenticate all components in the chain of components when the routine detects a power on condition and may authenticate only the newly connected component when the routine detects the connection of a component. As an example, the routine may authenticate all components when the system is first powered on and then may authenticate only newly connected patient protection devices when patient protection devices are replaced between treatments. Thus, the logic of block 606 may be skipped when the routine detects connection of a newly added component.

The routine may employ various mechanisms for authenticating components. Although some mechanisms are identified herein, one skilled in the art would recognize that various mechanisms exist for authenticating components. As an example, one such mechanism is a concept known as trusted computing. When using the trusted computing concept, transactions between every component are secured, such as by using encryption, digital signatures, digital certificates, or other security techniques. When a component connects to the system, the component may be queried (e.g., challenged) for its authentication credentials, such as a digital certificate. The component could then provide its authentication credentials in response to the query. Another component that sent the query can then verify the authentication credentials, such as by verifying a one-way hash value, a private or public key, or other data that can be used to authenticate the component. The authentication credentials or authentication function can be stored in a secure processor memory, or in other secure memory that is associated with the component that is to be authenticated. In some embodiments, a querying component can provide a key to a queried component, and the queried component can respond by employing an authentication function, such as a one-way hash function, to produce a responsive key, such as a one-way hash value. The queried component can then respond to the query by providing the produced responsive key to the querying component. The two components can thus authenticate each other to establish a secure communications channel. Further communications between the authenticated components can transpire over the secure communications channel by using encrypted or unencrypted data. Various known encryption techniques can be employed.

At decision block 610, the routine determines whether a component cannot be authenticated. As an example, the routine may detect whether any component in the chain of components could not be authenticated. If at least one of the components in the chain of components cannot be authenticated, the routine continues at block 612. Otherwise, the routine continues at block 616.

At block 612, the routine stores an indication in a log that the component(s) could not be authenticated and can report an error to the operator of the system. At block 614, the routine disables treatments so that the unauthenticated component cannot be used with the system. When the unauthenticated component is removed and another component is added that can be authenticated (e.g., starting at block 608), the system can continue treatments. The routine then continues at block 618, where it returns.

At block 616, the routine enables treatments so that when a treatment is started, appropriate action can be taken by the cooling device, such as based on selected treatment profiles. The routine then returns at block 618.

In some embodiments, the systems supports an authentication override feature. In these embodiments, an operator may request a manufacturer or distributor of the system for an authentication override key. Upon receiving this authentication override key, the operator can provide it to the system. The system may then operate with unauthenticated components for a defined period of time, such as 30 days. After expiry of this period of time, the system may need to receive code updates or other maintenance to again be able to enable the authentication override feature. In some embodiments, the operator may be able to override authentication a defined number of times with different authentication override keys before the system is updated or maintained to re-enable the authentication override feature. When the authentication override feature is enabled, the system can ignore authentication failures of some or all components of the system. As an example, an operator may need to use recently expired patient protection devices because new patient protection devices are not available. In such a case, the operator may override authentication until the new patient protection devices arrive.

Figure 7:
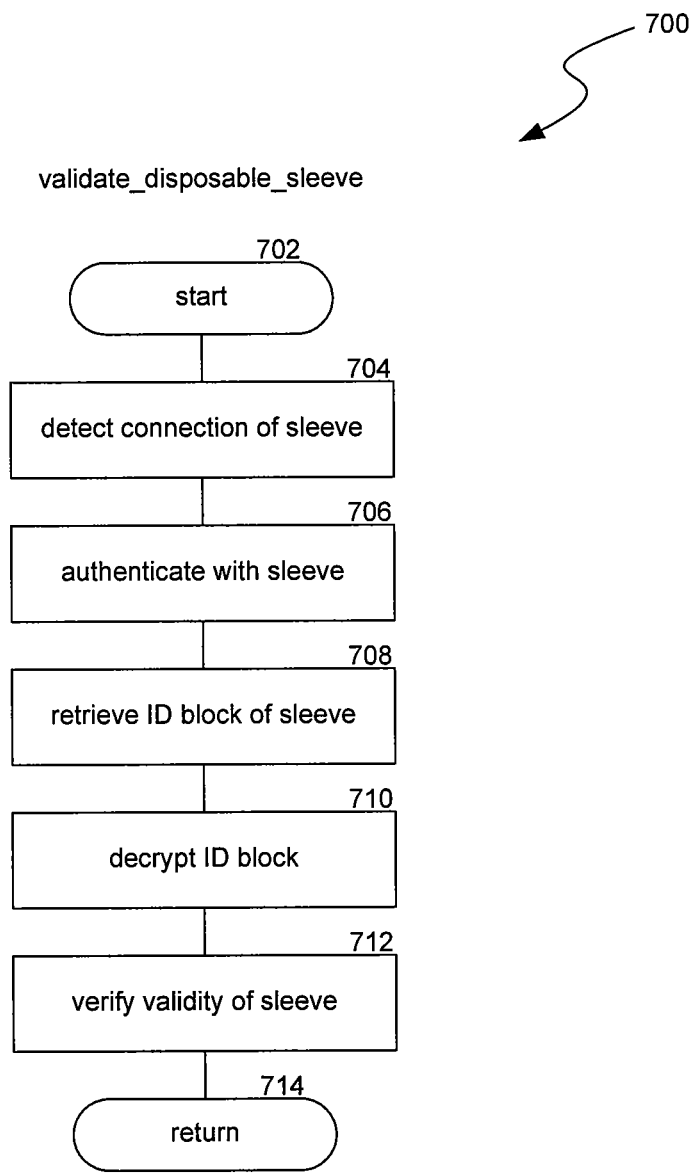
FIG. 7 is a flow diagram illustrating a validate_disposable_patient protection device routine invoked by the system in some embodiments.

FIG. 7 is a flow diagram illustrating a validate_disposable_patient protection device routine invoked by the system in some embodiments. The system can invoke the validate_disposable_patient protection device routine 700 to validate a newly connected patient protection device, such as when authenticating connected components (e.g., at block 608 of FIG. 6). The validate_disposable_patient protection device routine 700 begins at block 702.

At block 704, the routine detects the connection of a patient protection device. As an example, the routine may receive an indication that a patient protection device has been connected, such as from an applicator or a controller. The applicator may detect the connection of the patient protection device electronically or mechanically. The applicator may then provide an indication that a patient protection device has been connected, such as to a controller.

At block 706, the routine authenticates the remainder of the system with the newly connected patient protection device. Authentication of components was described above in relation to FIG. 6. The routine may employ the same authentication mechanisms or a different authentication mechanism to authenticate with the patient protection device.

At block 708, the routine retrieves an identification ("ID") block and a use block that are stored in a memory, such as a secure processor memory or in other secure memory that is associated with the newly connected patient protection device. The ID and use blocks are described above in relation to FIG. 4.

In various embodiments, the ID and/or use blocks may be encrypted. When the ID block is encrypted, the routine decrypts the ID block at block 710. The routine can also decrypt use blocks that are encrypted. Various encryption and decryption techniques are known in the art, such as encryption techniques that use public or private keys that can be symmetric or asymmetric. These encryption and decryption techniques can be applied via hardware and/or software.

At block 712, the routine verifies the validity of the newly connected patient protection device. The routine may employ various techniques to verify the validity of the newly connected patient protection device. The routine may ensure that the data stored in the fields of the retrieved ID block are valid, such as by verifying the stored patient protection device type and serial number. The routine may also compare an identifier (e.g., serial number) of the patient protection device to a list of patient protection devices that are known to be invalid or expired. The list of invalid patient protection devices may be provided by the operator of the system, manufacturer of the system, distributor of the system, or others. In some embodiments, the system may update the list of invalid patient protection devices from time to time automatically, such as by downloading the list via a network connection. The list can be stored in a memory or storage device, such as in a circular buffer or a table. The routine can also compare the use limit data from the ID block to the use data recorded in the use block to determine if the patient protection device is expired.

The routine then returns at block 714.

Figure 8:
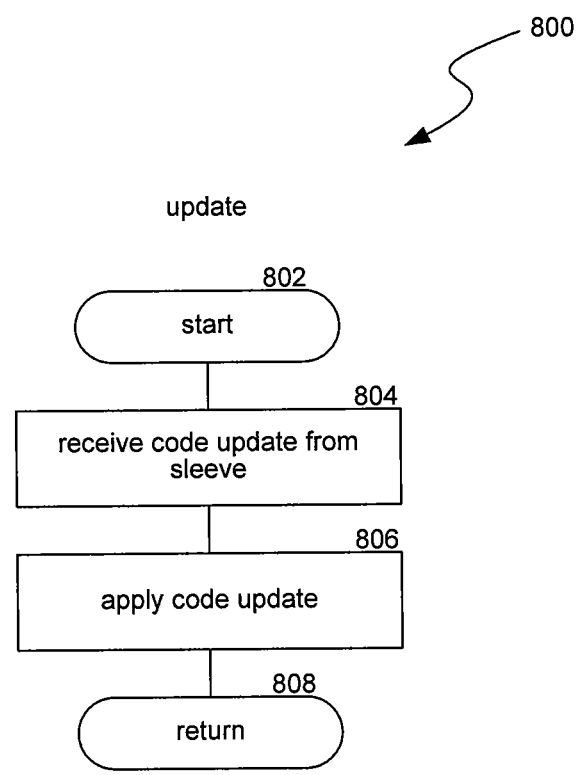
FIG. 8 is a flow diagram illustrating an update routine invoked by the system in some embodiments.

FIG. 8 is a flow diagram illustrating an update routine invoked by the system in some embodiments. The system may invoke the update routine when it receives code for updating updatable code of the system. As an example, the system may receive the code via a network connection or a patient protection device. Upon authenticating the source of the code, the system can apply the update. The update routine 800 begins at block 802.

At block 804, the routine receives a code update from a patient protection device. In some embodiments, the routine may receive an indication to update the code from the patient protection device and may then retrieve the code via a network connection, such as from a server. In some embodiments, the routine may also receive the indication to update the code from a server, an operator of the system, or other sources. The routine may then retrieve the code via a network connection or from another source, such as from a storage device that the system connects to. The routine may authenticate the source of the code update before retrieving the code.

At block 806, the routine applies the code update. As examples, the routine can apply the code update to a computing device, a controller, an applicator, or other component of the system that stores code. The component receiving the updated code may then need to be restarted, in which case the routine may cause that component to restart. At block 808, the routine returns.

E. User Interfaces

Figure 9:
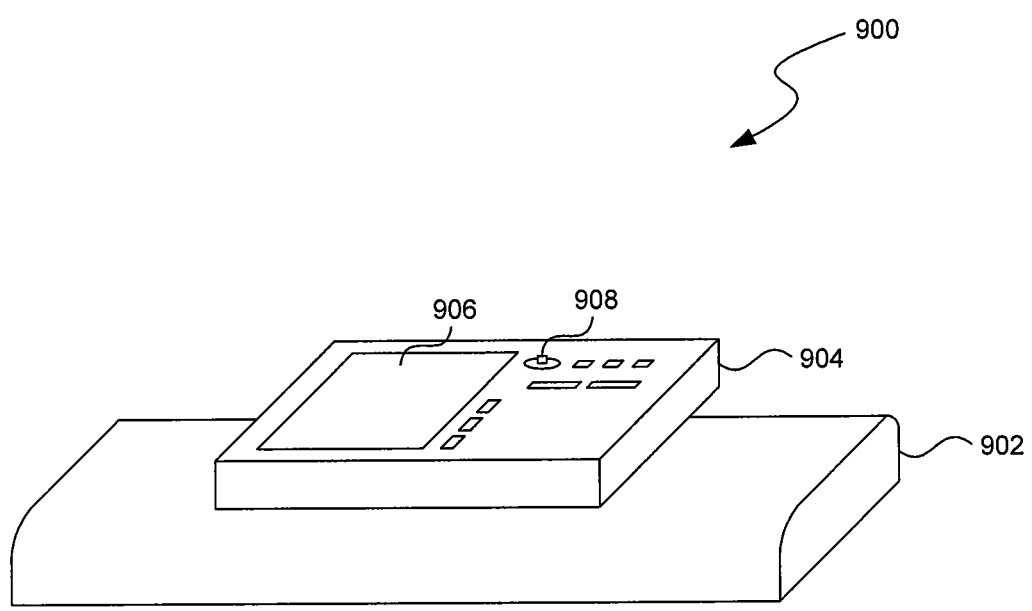
FIG. 9 is a front isometric view of an embodiment of an applicator.

FIG. 9 is a front isometric view of an embodiment of an applicator. In the illustrated embodiment, the applicator 900 includes an applicator portion 902 and a user interface portion 904. The applicator portion can include heat exchanging units, vibrators or massagers, vacuums, and connections to a controller, chiller, and other components of the system. These units and lines of connection are hidden in the illustrated front isometric view. The user interface portion 904 can include a display panel 906, such as a touch screen or other output device, and one or more input features, such as buttons or dials 908. In various embodiments, applicators have different sizes and shapes than the illustrated applicator 900. As examples, applicators can take the form of belts, handheld devices, and other devices of various sizes and shapes. In various embodiments, the user interface associated with an applicator can include various input and output devices, such as buttons, knobs, styluses, trackballs, microphones, touch screens, liquid crystal displays, light emitting diode displays, lights, speakers, earphones, headsets, and the like.

Figure 10A:
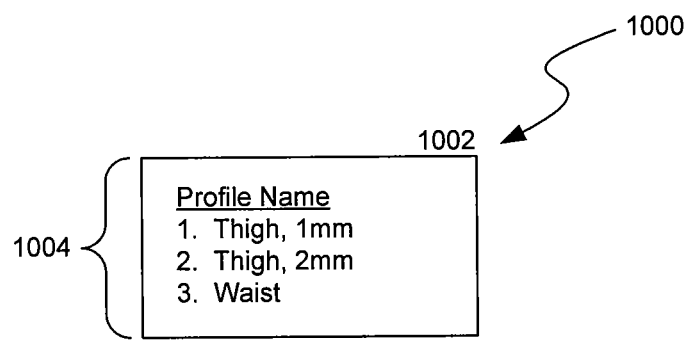
FIGS. 10A-10B are user interface diagrams illustrating aspects of user interfaces provided by the system in various embodiments.
Figure 10B:
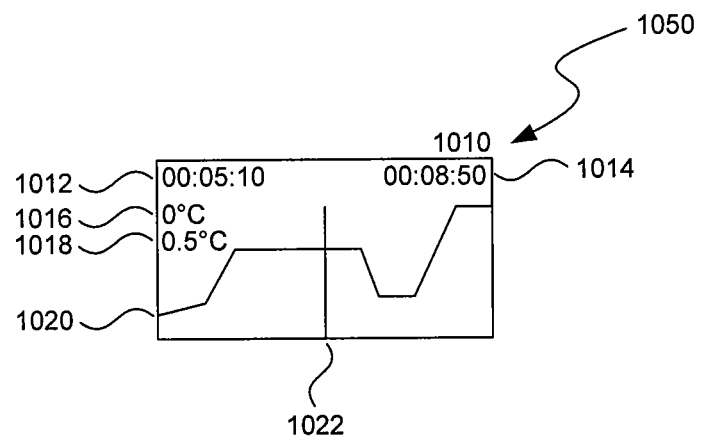

FIGS. 10A-10B are user interface diagrams illustrating aspects of user interfaces provided by the system in various embodiments. According to the user interface diagram 1000 illustrated in FIG. 10A, the system can display a list of treatment profiles 1004, test routines, or debugging/troubleshooting routines in a display 1002. The display 1002 can be displayed in a display panel 906 associated with an applicator (illustrated in FIG. 9) or on some other output device, such as an output device 120 (illustrated in FIG. 1). The list of treatment profiles 1004 can be retrieved from memory associated with a patient protection device. The operator of the cooling device can select one of the profiles to apply during treatment. As an example, the operator can select one treatment profile for one region of the subject's body and another treatment profile for another segment of the subject's body. The system can connect to multiple applicators in some embodiments, and each applicator can be applied in parallel.

In various embodiments, the operator can select other attributes that can cause the selected profile to be varied, such as the subject's characteristics (e.g., sex, weight, height, etc.) or subject's goals (e.g., amount of fat removal expressed in millimeters or percentages). The operator can also indicate other attributes, such as the subject's pain sensitivity, total number of treatments desired, and so forth. As an example, if the subject is available for many treatments, each treatment may need less time to administer.

According to the user interface diagram 1050 illustrated in FIG. 10B, the system can display various information during a treatment in a display 1010. The display 1010 can be displayed in a display panel 906 associated with an applicator (illustrated in FIG. 9) or on some other output device, such as an output device 120 illustrated in FIG. 1. The display 1010 can include a count-up timer 1012, a count-down timer 1014, target temperature 1016, actual temperature 1018, and a chart 1020. The count-up timer 1012 can count the elapsed time, such as the elapsed time of the treatment or the current treatment profile segment. The count-down timer 1014 can count the time remaining, such as the time remaining for the treatment or the current treatment profile segment. The target temperature 1016 can show the target temperature, such as for a selected heat exchanging unit or other portion of the applicator. The actual temperature 1018 can show the actual temperature at the region corresponding to the target temperature 1016 or at some other region. The chart 1020 can depict various information in a graphical form, such as a temperature vs. time chart. A marker 1022 can indicate the present time in relation to the chart so that an operator or subject can quickly see what actions the treatment profile will take or has taken. As an example, according to the illustration, the treatment profile will soon reduce the temperature for some time period and will subsequently increase the temperature.

In some embodiments, the system can take input from other devices. As an example, the system can receive an image, such as from an ultrasound device, and enable the operator or subject to indicate on the image how much fat should be removed. The controller can then determine the applicable treatment profile, such as based on the fat thickness and other attributes.

F. Conclusion

Various embodiments of the technology are described above. It will be appreciated that details set forth above are provided to describe the embodiments in a manner sufficient to enable a person skilled in the relevant art to make and use the disclosed embodiments. Several of the details and advantages, however, may not be necessary to practice some embodiments. Additionally, some well-known structures or functions may not be shown or described in detail, so as to avoid unnecessarily obscuring the relevant description of the various embodiments. Although some embodiments may be within the scope of the claims, they may not be described in detail with respect to the Figures. Furthermore, features, structures, or characteristics of various embodiments may be combined in any suitable manner. Moreover, one skilled in the art will recognize that there are a number of other technologies that could be used to perform functions similar to those described above and so the claims should not be limited to the devices or routines described herein. While processes or blocks are presented in a given order, alternative embodiments may perform routines having steps, or employ systems having blocks, in a different order, and some processes or blocks may be deleted, moved, added, subdivided, combined, and/or modified. Each of these processes or blocks may be implemented in a variety of different ways. Also, while processes or blocks are at times shown as being performed in series, these processes or blocks may instead be performed in parallel, or may be performed at different times. The headings provided herein are for convenience only and do not interpret the scope or meaning of the claims.

The terminology used in the description is intended to be interpreted in its broadest reasonable manner, even though it is being used in conjunction with a detailed description of identified embodiments.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. When the claims use the word "or" in reference to a list of two or more items, that word covers all of the following interpretations of the word: any of the items in the list, all of the items in the list, and any combination of the items in the list.

Aspects of the technology may be stored or distributed on computer-readable media, including magnetically or optically readable computer discs, hard-wired or preprogrammed chips (e.g., EEPROM semiconductor chips), nanotechnology memory, biological memory, or other data storage media. Indeed, computer implemented instructions, data structures, screen displays, and other data under aspects of the technology may be distributed over the Internet or over other networks (including wireless networks), on a propagated signal on a propagation medium (e.g., an electromagnetic wave(s), a sound wave, etc.) over a period of time, or they may be provided on any analog or digital network (packet switched, circuit switched, or other scheme). Those skilled in the relevant art will recognize that portions of the technology reside on various computing devices, such as a server computer, a client computer, and so forth. Thus, while certain hardware platforms are described herein, aspects of the technology are equally applicable to nodes on a network or other types of computing devices.

Any patents, applications and other references, including any that may be listed in accompanying filing papers, are incorporated herein by reference. Aspects of the described technology can be modified, if necessary, to employ the systems, functions, and concepts of the various references described above to provide yet further embodiments.

These and other changes can be made in light of the above Detailed Description. While the above description details certain embodiments and describes the best mode contemplated, no matter how detailed, various changes can be made. Implementation details may vary considerably, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the claims to the specific embodiments disclosed in the specification, unless the above Detailed Description section explicitly defines such terms. Accordingly, the actual scope of the claims encompasses not only the disclosed embodiments, but also all equivalents.

We claim:

1. A system for changing a temperature of a subcutaneous lipid-rich region of a subject having a skin, comprising:
    an applicator having:
        a heat exchanging surface configured to reduce a temperature of the lipid-rich region; and
        a first memory component;
    an applicator accessory removably and physically connectable to the applicator and having a second memory component; and a controller that receives authentication information for the applicator from the first memory component, receives authentication information for the applicator accessory from the second memory component, and allows or prevents the applicator from changing the temperature of the lipid-rich region based on the authentication information for the applicator and the authentication information for the applicator accessory.

2. The system of claim 1 further comprising:
a chiller that removes heat from a coolant, and
a supply line that carries coolant from the chiller to the applicator.

3. The system of claim 1 further comprising a computing device that commands the controller to apply a treatment based on a treatment profile, wherein:
the second memory component stores the treatment profile, and
the treatment profile indicates a temperature to which the lipid-rich region is to be cooled and a duration during which the lipid-rich region is to maintain the indicated temperature.

4. The system of claim 3 further comprising a data acquisition device that collects data from the applicator and provides the collected data to the computing device.

5. The system of claim 3 wherein:
the computing device provides a user interface to enable an operator to select the treatment profile from multiple treatment profiles, and
the multiple treatment profiles are identified in the second memory component.

6. The system of claim 3 wherein the computing device connects to a data communications network to retrieve a list of invalidated applicator accessories.

7. The system of claim 3 wherein the computing device connects to a data communications network to provide a list of applicator accessories that have expired.

8. The system of claim 1 wherein:
the applicator provides a user interface to enable an operator to select a treatment profile from multiple treatment profiles, and
the multiple treatment profiles are identified in the second memory component.

9. The system of claim 1 wherein the controller and the applicator accessory are configured to authenticate each other.

10. The system of claim 1 wherein the first memory component is a secure memory component.

11. The system of claim 1 wherein the first memory component is a portion of a secure processor.

12. The system of claim 1 wherein the controller retrieves authentication information for the applicator accessory in response to connecting the applicator accessory to the applicator.

13. The system of claim 1 wherein the controller receives usage information from the second memory component, and allows or prevents the applicator from changing the temperature of the lipid-rich region based at least in part on the usage information.

14. The system of claim 1 wherein the applicator detects connection of the applicator accessory electrically.

15. The system of claim 1 wherein the applicator detects connection of the applicator accessory mechanically.

16. The system of claim 1 wherein the second memory component stores a treatment profile.

17. The system of claim 1 further comprising:
a computing device, and
a temperature sensor, wherein the computing device receives a temperature indication from the temperature sensor and commands the controller to control the applicator based on the temperature indication.

18. The method of claim 17 wherein the controller controls power to the applicator to adjust the temperature.

19. The system of claim 1 wherein the second memory component stores:
a use block including information relating to use of the applicator accessory, and
an identifier block including a limit value for use of the applicator accessory.

20. The system of claim 19 wherein:
the applicator accessory is configured for limited use, and
when the use block indicates that the limit value has been reached, the applicator will not change the temperature of the lipid-rich region when used with the applicator accessory.

21. The system of claim 1 wherein:
the controller has a third memory component, and
the applicator receives authentication information for the controller from the third memory component, receives authentication information for the applicator accessory from the second memory component, and is enabled or disabled from changing the temperature of the lipid-rich region based on the authentication information for the controller and the authentication information for the applicator accessory.

22. The system of claim 21 wherein the applicator accessory receives authentication information for the applicator from the first memory component, receives authentication information for the controller from the third memory component, and allows or prevents the applicator from changing the temperature of the lipid-rich region based on the authentication information for the applicator and the authentication information for the controller.

23. The system of claim 21 wherein the first, second, and third memory components are secure memory components.

24. The system of claim 21 wherein the first, second, and third memory components are portions of secure processors.

25. The system of claim 1 wherein:
the second memory component stores a treatment profile including a dwell time and a target temperature,
the target temperature indicates a target temperature for the lipid-rich region, and
the dwell time indicates a time during which the lipid-rich region should be kept at or near the target temperature.

26. The system of claim 25 wherein the treatment profile includes multiple segments individually indicating a dwell time and a target temperature.

27. The system of claim 26 wherein the segments individually indicate a ramp time during which temperature is reduced or increased so that the target temperature indicated in the segment is reached when the ramp time ends.

28. The system of claim 27 wherein the temperature is reduced or increased according to a transfer function.

29. The system of claim 28 wherein the transfer function is proportional integral derivative.

30. The system of claim 29 wherein the applicator cycles through the target temperatures of each segment.

* * * * *

UNITED STATES PATENT AND TRADEMARK OFFICE
CERTIFICATE OF CORRECTION

PATENT NO. : 8,523,927 B2  
APPLICATION NO. : 11/777992  
DATED : September 3, 2013  
INVENTOR(S) : Levinson et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1751 days.

Signed and Sealed this  
Seventh Day of April, 2015

Michelle K. Lee  
*Director of the United States Patent and Trademark Office*

UNITED STATES PATENT AND TRADEMARK OFFICE
CERTIFICATE OF CORRECTION

| | |
|---|---|
| PATENT NO. | : 8,523,927 B2 |
| APPLICATION NO. | : 11/777992 |
| DATED | : September 3, 2013 |
| INVENTOR(S) | : Levinson et al. |

It is certified that error appears in the above-identified patent and that said Letters Patent is hereby corrected as shown below:

On the title page, item (56)

On page 4, in column 1, under "Other Publications", line 4-5, delete "breat tissue:" and insert -- breast tissue: --, therefor.

On page 4, in column 1, under "Other Publications", line 12, delete "execretion" and insert -- excretion --, therefor.

On page 4, in column 1, under "Other Publications", line 12, delete "mahnesium," and insert -- magnesium, --, therefor.

On page 5, in column 1, under "Other Publications", line 12, delete "Hivermales,"" and insert -- Hivernales," --, therefor.

On page 5, in column 1, under "Other Publications", line 26, delete "Cryprobe."" and insert -- Cryoprobe," --, therefor.

On page 5, in column 1, under "Other Publications", line 37, delete "Pathogensesis" and insert -- Pathogenesis --, therefor.

In the claims

Column 16, line 63, claim 1, delete "region;" and insert -- region, --, therefor.

Column 18, line 7, claim 18, delete "method" and insert -- system --, therefor.

Signed and Sealed this
Tenth Day of November, 2015

Michelle K. Lee
*Director of the United States Patent and Trademark Office*